(12) United States Patent
Chen et al.

(10) Patent No.: US 7,427,663 B2
(45) Date of Patent: Sep. 23, 2008

(54) CARDIO MYOPEPTIDIN, THE PRODUCTION AND THE USE THEREOF

(75) Inventors: Yusong Chen, Dalian (CN); Shu Li, Dalian (CN)

(73) Assignee: Dalian Zhen-Ao Pharmaceutical Co., Ltd., Dalian, Liaoning Province (CN)

( * ) Notice: Subject to any disclaimer, the term of this patent is extended or adjusted under 35 U.S.C. 154(b) by 160 days.

(21) Appl. No.: 10/567,286

(22) PCT Filed: Feb. 23, 2004

(86) PCT No.: PCT/CN2004/000138

§ 371 (c)(1),
(2), (4) Date: Feb. 3, 2006

(87) PCT Pub. No.: WO2004/108751

PCT Pub. Date: Dec. 16, 2004

(65) Prior Publication Data

US 2007/0117745 A1     May 24, 2007

(30) Foreign Application Priority Data

Jun. 4, 2003  (CN)  ................. 03 1 37133
Jun. 4, 2003  (CN)  ................. 03 1 41352

(51) Int. Cl.
*C07K 14/00* (2006.01)

(52) U.S. Cl. ...................... 530/385; 530/350

(58) Field of Classification Search ................. 530/350, 530/385; 514/2
See application file for complete search history.

(56) References Cited

FOREIGN PATENT DOCUMENTS

CN    1108663 A    9/1995

OTHER PUBLICATIONS

International Search Report dated Jun. 3, 2004 for PCT Application PCT/CN2004/000138.
Pharmaceutical Biotechnology, 1996, vol. 3(2); 98-100, Zhang Xiujian "Studies on Biochemical Characters and Effect on DNA Synthesis of Myocardial Cells of Heart Active Factor".

*Primary Examiner*—Karen Cochrane Carlson
(74) *Attorney, Agent, or Firm*—James P. Muraff; Neal, Gerber & Eisenberg LLP

(57) ABSTRACT

The present invention relates to a cardio myopeptidin which is isolated from the hearts of non-human healthy mammals. The molecular weight of the cardio myopeptidin is less than 10000 Dalton, the peptide content thereof being 75%~90%, the free amino acid content 6%~15%, the ribonucleic acid content less than 2%, and the deoxyribonucleic acid content less than 7.5%. The present invention further provides a method of producing the cardio myopeptidin and the use thereof in producing pharmaceuticals for treating cardiac disorders, specifically the use in producing pharmaceuticals for treating myocardial ischemic and reperfusion injury. The cardio myopeptidin of the present invention can work directly on myocytes, promoting the repair of injuries caused by various reasons, and providing a new way to relieve ischemic and reperfusion injury, and to promote the repair of injured myocardium.

8 Claims, 9 Drawing Sheets

| NO. | ARSCISSA | PEAK | HEIGHT | ABSCISSA | VALIEY | HEIGHT |
|---|---|---|---|---|---|---|
| 1 | 247.4 | 0.2884 | 0.0239 | 238.8 | 0.2818 | -0.4106 |
| 2 | 200.4 | 2.4966 | 1.4000 | | | |

```
==================================================================
                        Area Percent Report
==================================================================
```

Sorted By        :    Signal
Multiplier       :    1.0000
Dilution         :    1.0000

Signal 1: DAD1 A, Sig=254,10 Ref=360,100

| Peak # | RetTime [min] | Type | Width [min] | Area [mAU*s] | Height [mAU] | Area % |
|---|---|---|---|---|---|---|
| 1 | 1.320 | VV | 0.2476 | 523.23895 | 28.84586 | 2.3415 |
| 2 | 1.990 | VV | 0.0687 | 3608.51245 | 742.13055 | 16.1483 |
| 3 | 2.233 | VV | 0.1214 | 127.18691 | 14.92828 | 0.5692 |
| 4 | 2.491 | VV | 0.1013 | 371.21744 | 55.99518 | 1.6612 |

CARDIO MYOPEPTIDIN, THE PRODUCTION AND THE USE THEREOF

CROSS-REFERENCE TO RELATED APPLICATIONS

This application is a U.S. national stage application under 35 U.S.C. § 3.71 of international stage application number PCT/CN2004/000138, filed Feb. 23, 2004, which claims priority of Chinese patent application serial nos. 03137133.7, filed Jun. 4, 2003, and 03141352.8, filed Jun. 4, 2003.

TECHNICAL FIELD

The present invention relates to a myocardial polypeptide, the method for preparation and the use thereof. More specifically, this invention relates to a myocardial polypeptide (cardio myopeptidin) isolated from the hearts of healthy mammals other than a human, the method for manufacture and the use thereof. The present invention belongs to the field of biochemistry.

BACKGROUND OF THE INVENTION

"Myocardial protection" has been a hot subject in studies conducted by cardiac medicine and cardiac surgery in recent years. Recent documents showed that, ischemia and hypoxia could cause many changes to the myocardial cells, including overload of calcium in the cells, generation of free radicals, valvular injury, decrease in ATP (adenosine triphosphate, ATP) level, oxygen exhaustion, etc.

The consummation and popularization of cardiac surgical interventions have released numerous patients from pains and improved their life quality. With the increasingly higher requirements of people for myocardial protection, a lot of people have been in fundamental and clinical studies. The myocardial protection in clinical cardiac surgery includes myocardial protection prior, during and after the surgical operation, yet the focus is still on the prevention of ischemia and reperfusion injury in the course of extracorporeal circulation for cardiac arrest. For this purpose, the fundamental and clinical researchers have been aggressively tackling the issues of myocardial protection, which mainly include: (1) the way of perfusion, for example, direct perfusion, inverse perfusion, simultaneous perfusion, intermittent perfusion or continuous perfusion; and whether a blood cell filter is used, and so on; (2) temperature of the perfusate: mainly including normal temperature, low temperature, etc.; (3) components of the perfusate: such as the additional use of the oxygen free-radical scavenging of super-oxide dismutase, reduced glutathione, aprotinin, or puerarin, etc. These measures have, to a certain degree, changed the pathological processes of the myocardial ischemia-reperfusion injury. Some foreign researchers tried to put phosphokinase (Neoton from Italian OUHUI Pharmaceutical Plant) in the perfusate or have patients take trimetazidine dihydrochloride (Vasorel from French Servier), so as to improve the metabolism of cardiac muscle, and elaborated some of their findings from aspects of cell, subcellular structure, oxygen free radicals, energy metabolism, calcium ion ($Ca^{2+}$) overload and so on. However, these studies either focused only on the supplement of energy or separated the prevention of damage from the defense mechanism of the organism itself, which led to the unsatisfactory clinical outcome in preservation of the cardiac myocardium. Therefore, it is necessary to research and develop more efficacious therapeutic agents for myocardial protection.

In order to interfere with myocardial ischemia and protect heart muscle, many drugs were developed in the past twenty years, such as β-blockers, calcium antagonists, converting enzyme inhibitosr, various oxygen free-radical scavengers etc, but their protective effect on cardiac muscle is not affirmed clinically yet. None of the existing medicine for the treatment of myocardial ischemia can absolutely decrease myocardial infarction and antagonize myocardial ischemia. The alteration in the salivary gland chromosome of the fruit fly *Drosophila* following a short-term elevation in the temperature was reported in the late 1980s, indicating genetic transcription was activated, which was called heat shock reaction (HSR, Anna Rev Biochem 1986, 55:1151). Thereafter, it was found that the heat shock preconditioning of experienced animals could obviously decrease damage to the myocardium caused by ischemia/perfusion, and it was named "ischemia precondition" (IP) by Marry in 1986. Further research indicated that a new group of proteins, that is heat shock proteins ($HSP_S$), or so-called stress proteins (SP), were induced and synthesized by heat shock of cardiac myocytes. These successive research reports demonstrated that heart muscle itself has strong cellular tolerance; later, it was found that $HSP_S$ can be induced and expressed under the heat shock treatment for both cultured cells and the whole organism, such as prokaryotes, eukaryotes, plants, animals and human beings. The features of HSR and $HSP_S$ is shown as following: (1) Besides induction by heat shock, HSP could be synthesized by many other factors, such as ischemia, hypoxia, ethanol, heavy metallic salt, myocardial pressure load, drugs and most disease, and could produce "cross tolerance phenomenon". (2) HSP had high conservatism in structure; for example, 72% of amino acid sequence of $HSP_{70}$ is identical for fruit fly and saccharomycete, 73% of $HSP_{70}$ gene is homologous for human and fruit fly, and 78% for $HSP_{90}$. These structural similarities guaranteed the functional sameness (Burdon: Biochem, J. 1986, 240:313). (3) HSP had an optimum time horizon on myocardial protection, alternatively called "window of opportunity," and it would not provide protection if a certain time limit was exceeded (Perdriget: Curr. Surg., 1989, 23). (4) HSP existed in the whole biological universe and was present in various cells of organisms of higher animals. Induction of $HSP_S$ not only enhances rehabilitation of myocardial function, but also reinforces rehabilitation of myocardial endothelial function and extends the cardioplegic arrest time. The above described function can be used in donor protection of heart transplantation, salvage of myocardium ischemic, preparation of cardioplegic solution for extracorporeal circulation, etc., and it can break through the restriction of traditional drugs and provide a milestone new method that starts from enhancing the induction of self anti-damage potential of in-vivo cells.

Pennica et al (1995) cloned the cardiotrophin-1 (CT-1) gene from myocardial cells, and expressed it in *Escherichia coli*. It was indicated that CT-1 is a type of cytokine with the function of immunoloregulation, induction of proliferation, and anti-injury of myocardial cells caused by hypoxia and high temperature. It naturally exists in the myocardial cells and can inhibit the apoptosis of myocardial cells. Further research showed that CT-1 could induce HSP expression in cultured myocardial cells and in vivo. The effect of induction is concerned with a cell surface polypeptide named $gp^{130}$, and the activated $gp^{130}$ reinforces the expression of $HSP_{70}$, $HSP_{90}$ and micromolecule substrate of HSP through NF-IL-6/NF-IL-6β and tyrosine kinase path, thus enhancing the ability of the myocardial cells to tolerate hypoxia and high temperature. Studies also indicated that CT-1 could promote synthesis of structural protein of the myocardial cells, and the increase in the long axis of cells could make contraction stronger. The study of myotrophin of gene recombination is another subject of stimulating factors of the myocardial cells. Parames (1997) demonstrated that myotrophin promotes growth of the myocardial cells and is associated with protein kinase-C. Myotrophin and cardiotrophin may all be cytokines with similar function in the myocardial cells and different paths to activate cellular proliferation, and both show the function of protecting the myocardial cells and promoting proliferation.

Among the available cardiovascular drugs, except for converting enzyme inhibitor which has the function of blocking the generation of growth factors, inhibiting protein synthesis and myocardial hypertrophy, other drugs do not have the function of regulating the growth, differentiation and rehabilitation of cardiac muscles. In recent years, inducing the protection of cardiac muscle cells themselves by pharmacological treatment has been emphasized overseas, such as the research on promoting the myocardial regeneration by transduction gene etc, and the study on cardiotrophin and myotrophin. Moreover, extracellular signals are used to trigger various transmission mechanisms and to regulate and control the proliferation or reconstitution of myocardial and vascular cells. However, all of this research is at the stage of animal testing or preclinical study.

It is clearly demonstrated from aforesaid studies that, in the situation where protection of cardiac muscle for extracorporeal circulation is not consummated yet, it is of great importance to provide a drug that poses no damage to the organism and can protect cardiac muscle prior, during and after surgical interventions. A new approach to explore the prevention and cure of myocardial ischemia and reperfusion injury is also necessary.

ZL94102798 disclosed a growth-stimulating peptide of the myocardial cells and the process for preparation thereof. The process comprises the steps of: the heart of healthy infant mammals other than a human was crushed with mechanical means, deep frozen at −20° C. and heated to 60-100° C. after dissolving in water, then deep frozen at −20° C. and centrifuged at 3000 rpm after being melted, and finally a polypeptide active substance with molecular weight less than 20000 Da was obtained through negative pressure interception column, sterilization, filling, lyophilization and packing.

ZL94102799 disclosed a growth-stimulating peptide of the myocardial cells (GMGSP) that can stimulate DNA synthesis and protein synthesis of primarily cultured myocardial cells, which was isolated from the heart of healthy infant mammals other than a human mammal, and stabilizes at pH 2-9; the biological activity did not change when GMGSP was heated at 95-100° C. for 10 minutes or at 60-70° C. for 30 minutes, but biological activity was lost when being placed in proteolytic enzymes at 37° C. for two hours; a polymer was formed at 22° C.-30° C. in aqueous solution, but biological activity did not have obvious change; biological activity did not change if GMGSP was lyophilized and sealed with 3%-8% mannitol and stored at room temperature for 1.5 years, or at 4° C. for 2 years, or at −20° C. for 3 years; HPLC analysis indicated that the aforesaid GMGSP is composed of four components. The relative peaks and retention times of each component were respectively 10.4% (2.88 minutes), 6.4% (3.93 minutes), 36.3% (5.09 minutes) and 7.3% (7.41 minutes), and each component has biological activity. The molecular weights of two bands displayed by SDS-PAGE analysis were respectively 8500 Da and 10800 Da. The average molecular weight displayed by HPLC analysis was 9800 Da, average molecular weight was 10500 Da, and both components have biological activity.

However, the biologically active peptides described in above-mentioned patents are obtained by a rough separation, purification, the test of activity is also simple, and it fails to provide detailed description for its ingredients, use and efficacy.

SUMMARY OF THE INVENTION

The first object of the present invention is to provide a cardio myopeptidin. The major active ingredient of cardio myopeptidin is a polypeptide, which can act on the myocardial cell directly and promote the repair of myocardial damage caused by multiple factors. This invention provides a new approach to decrease myocardial damage in cardiac surgery and promote repair of damage.

The second object of the present invention is to provide an improved process for the preparation of cardio myopeptidin. The process is simple and the product obtained has moderate molecular weight, high purity and good stability. Although the color of said product will change into light yellow after storage for 480-540 days, other properties will remain unchanged.

The third object of the present invention is to provide the use of cardio myopeptidin for the manufacture of a medicament for the treatment of cardiovascular disease.

The fourth object of the present invention is to provide the use of cardio myopeptidin for the manufacture of a medicament for the treatment of myocardial ischemia-reperfusion injury.

According to one aspect of the present invention, there is provided a cardio myopeptidin, which is a polypeptide isolated from hearts of healthy non-human mammals. The peptide content thereof is 75%~90%, the free amino acid content is 6%~15%, the ribonucleic acid (RNA) content is less than 2%, the deoxyribonucleic acid (DNA) content is less than 7.5%, and the average molecular weight is less than 10000 Da.

The above-mentioned healthy non-human mammals comprise pigs, cattle, sheep, rabbits, horses and so on. It is preferred the infant mammals are chosen from pigs, cattle, sheep, rabbits, horses etc. Infant pigs are more preferred.

The average molecular weight of cardio myopeptidin is less than 10000 Da, preferably in the range from 1000 to 10000 Da, more preferably in the range from 2000 to 8000 Da, and the most preferably in the range from 2000 to 5000 Da.

The biological activity of cardio myopeptidin is stable at pH from 3 to 8. The cardio myopeptidin is sensitive to protease K. The biological activity will not change at the temperature of 85° C. for 10 minutes, and is stable under frozen or lyophilized conditions.

Isoelectrofocusing electrophoresis of cardio myopeptidin displays 2~6 stained bands. It is preferred that isoelectrofocusing electrophoresis displays two bands, among which the band whose pI is 10.92 is the one with deeper color.

The cardio myopeptidin of the present invention has a stable maximum absorption peak at 190~210 nm wavelength in the UV spectrum. It is preferred the maximum ultraviolet absorption peak is at 200±2 nm wavelength.

Sulfosalicylic acid reagent test indicates that no protein is contained in the cardio myopeptidin of the present invention.

The activity of the cardio myopeptidin of the present invention is at least 2.2.

The cardio myopeptidin of the present invention further comprises excipient, and the content by weight is: cardio myopeptidin: 15~20, excipient: 100~375. Above which, it is preferred the content is 18~20: 200~375. The excipient may be mannitol, trehalose, lactose, sucrose or other adjuvants for lyophilization, preferably mannitol.

In order to depyrogenate, the cardio myopeptidin may further comprise activated carbon with the content from 0.05% to 0.1%.

The cardio myopeptidin of this invention principally showed five peaks on FPLC analysis spectrum, and the sum of relative area is 90%~95%. An activity test indicates that the five peaks can all promote the activity of succinic dehydrogenase of primarily cultured myocardial cells and the myocardial cells with oxygen re-supplied due to lack of oxygen, among which the activity of peak P1 is comparatively high.

The present invention also provides a method for preparing the cardio myopeptidin, which comprises the steps of:
(a) cleaning and cutting the hearts of hearts of healthy non-human mammals;
(b) homogenizing by adding sterile distilled water to the myocardium of healthy non-human mammal which is cleaned and cut;
(c) freezing and thawing cycles of the homogenate alternately for 3 or 4 times;
(d) filtering by the plate-and-frame filter to get a coarse filtrate and removing the residue after the homogenate is heated to 65~95° C.;
(e) ultra-filtering the coarse filtrate with a hollow-fiber column to get a fine filtrate;
(d) ultra-filtering the fine filtrate by ultrafiltration membrane to intercept the cardio myopeptidin solution with the molecular weight less than 10000 Da;
(e) concentrating the solution by reverse osmosis to get a concentrated cardio myopeptidin solution.

The method may further comprise the steps of testing the quality, filtering aseptically, filling and lyophilizing.

The amount of sterile distilled water added is from 0.5 to 4 times of that of the myocardium of mammals, and the rotation speed of homogenization is in the range from 1000 to 5000 rpm/min.

The freezing is performed at a temperature of less than −5° C. for 24~72 hours, preferably at −20° C.~−30° C. for 36~48 hours; heating is in the way of water bath heating or direct heating at a temperature of 70~90° C. for not more than 2 hours, and preferably water bath heating at a temperature of 75° C.~80° C. for 1 hour.

In the present invention, the coarse filtrate is obtained through a plate-and-frame filter, fine filtrate with molecular weight less than 12 k Da is obtained through a hollow fiber column, and final filtrate with molecular weight less than 10 k Da is obtained by intercepting part of solution through ultrafiltration membrane. The plate-and-frame filter is conventional biopharmaceutical equipment with the medium-speed filter paper having pores less than 10μ, preferably the pores less than or equal to 5μ, such as the XAS03-172/8 model plate-and-frame filter manufactured by Guangzhou Medicinal Apparatus Research Institute. F60 model hollow fiber column which can filter liquid with a molecular weight less than 12 k Da is introduced, such as hollow fiber columns produced by Sweden Gambro. The specification of the ultrafiltration membrane is 1~10 k Da, such as the products of Millipore Corporation, and the reverse osmosis/concentration column is also the product of Millipore Corporation.

The aseptic filtration and filling processes described in the present invention are prior art and are well known by a person skilled in the art.

The current lyophilizer is introduced for freeze-drying the cardio myopeptidin in the present invention. The process of lyophilization comprises the steps of: the shelf in the drying chamber is cooled down to the temperature of −15° C.~−20° C. in 5~40 minutes, preferably to −18° C.~−20° C. in 20~30 minutes, followed by the cardio myopeptidin being frozen to the temperature of −25~−35° C. within 20~40 minutes and maintaining at this temperature for 1~3 hours, preferably to −30~−35° C. within 25~35 minutes; then the condenser is chilled to the temperature of −40~−50° C. At that time, the pressure is reduced till the vacuum degree reaches 90~100 Kpa, the drying chamber is connected with condenser, and the refrigeration is stopped. After that, the temperature of drying chamber is raised to 5~15° C. at the rate of 2~5° C./min and maintained at this temperature for 3~6 hours when the vacuum degree of the drying chamber gets to 10~15 Pa, preferably the temperature is ascended to 8~12° C. at the rate of 3~4° C./min with 4~5 h heat preservation. The temperature is elevated continuously to 15~25° C. at the rate of 8~16° C./min and kept for 3~8 hours, preferably the temperature is raised to 18~22° C. at the rate of 10~12° C./min for 4~6 hours. Then the temperature is further increased continuously to 30~35° C. at the rate of 7~15° C./min and maintained for 1~4 hours, preferably 33~35° C. at the rate of 9~12° C./min for 1.5~2 hours. Furthermore, the temperature is raised continuously to 50~60° C. at the rate of 4~8° C./min lasting for 1~3 hours, preferably to 54~58° C. at the rate of 5~7° C./min for 1.5~2 hours. Then comes the cooling stage, in which the temperature is cooled down to 40-50° C. within 10~30 minutes and stands at such temperature for 8-15 hours, preferably cooled down to 45~48° C. in 15~20 minutes and 9~12 h preservation at such temperature to attain lyophilized production of cardio myopeptidin with qualified appearance.

In the process of preparing the cardio myopeptidin of this invention, a known adjuvant for lyophilized product may be introduced to the cardio myopeptidin solution, such as mannitol, trehalose, lactose, sucrose or other adjuvant as the auxiliary for lyophilization; the addition of adjuvant makes it easy to form a crystal lattice, which works as a bracket and stabilizes the product.

The cardio myopeptidin with the molecular weight less than 10000 Da can be obtained by filtering with a plate-and-frame filter, ultrafiltration with a hollow fiber column and ultrafiltration membrane respectively, and concentrating with reverse osmosis according to the process of this invention. Compared with the process described in ZL94102798 in the background, the process of the present invention enables a short operating time to obtain a large quantity of products with high concentration and activity but without pyrogen.

Furthermore, the present invention provides the use of cardio myopeptidin for the manufacture of a medicament for the treatment of cardiovascular disease.

Moreover, the present invention provides the use of cardio myopeptidin for the manufacture of a medicament for the treatment of myocardial ischemia-reperfusion injury.

The common dose of the lyophilized cardio myopeptidin of this invention for intravenous drip (infusion) is 0.1~2.0 mg/kg body weight, or following medical orders.

Compared with the growth-stimulating peptide of the myocardial cells (GMGSP) disclosed in Chinese patents ZL94102798 and ZL94102799, cardio myopeptidin of the present invention has obviously higher in vitro biological activity. The biological activity of cardio myopeptidin of the present invention is 3~5 times higher than that of the growth-stimulating peptide of the myocardial cells. Comparison data of in vivo drug efficacy shows that cardio myopeptidin poses a favorable impact on the release of myocardial creatine phosphokinase caused by myocardial ischemia-reperfusion injury, activity of lactate dehydrogenase, and contents of free fatty acid and malondialdehyde (MDA).

Cardio myopeptidin of this invention can directly act on myocardial cells and promote the repair of myocardial damage caused by multiple damage factors (such as ischemia, drug intoxication etc), and is a drug for promoting protein synthesis, reducing damage of oxygen free radicals, decreasing overload of calcium, inducing endogenous protection and improving the myocardial metabolism. The present invention provides a new approach to lessen the myocardial damage in cardiac surgical operations and promote the repair of injury.

Main pharmacodynamic and pharmacological findings of cardio myopeptidin of this invention are as follows:

1. Cardio myopeptidin can obviously lessen the damage of the myocardial ultrastructure caused by myocardial ischemia-reperfusion and make it approach or return to normal condition (FIG. 6-12 black-and-white photo and Table 13).
2. It is demonstrated by the electrocardiogram of epicardium that cardio myopeptidin can obviously antagonize ST elevation caused by myocardial ischemia in cats and reduce the scope of myocardial ischemia (Table 14-15).
3. Cardio myopeptidin can obviously lower the release of myocardial creatine phosphokinase caused by myocardial ischemia-reperfusion injury, increase the activity of lactate dehydrogenase, and enhance the contents of free fatty acid and malondialdehyde (Table 16-21).
4. The oxygen consumption of cardiac muscles can be reduced by cardio myopeptidin (Table 22).
5. ST and/or NST in the electrocardiogram of pigs with myocardial infarction can be significantly reduced or decreased by administering cardio myopeptidin at a dose of 5 mg/kg or 10 mg/kg per body weight, and the scope of myocardial infarction can also be reduced. Cardio myopeptidin has certain therapeutic effects on arrhythmia and ventricular fibrillation (they may cause death) in pigs with acute myocardial ischemia, but has no evident impact on blood pressure and heart rate (Table 23 and FIG. 13).

BRIEF DESCRIPTION OF THE DRAWINGS

To understand the present invention, it will now be described by way of example, with reference to the accompanying drawings in which.

DETAILED DESCRIPTION

The following preferred embodiments further describe this invention, and said preferred embodiments are only used to describe instead of limit this invention.

EXPERIMENTAL EXAMPLE 1

This experiment relates to the physicochemical property, purity, content and activity test of cardio myopeptidin solution.

1. Physicochemical property, purity and content of cardio myopeptidin solution.

Cardio myopeptidin of this invention is a small molecular active polypeptide, and its biological activity is stable at pH 3~8 and is not changed at 85° C. for 10 minutes. Cardio myopeptidin is sensitive to protease K and is stable under frozen or lyophilized condition. The average molecular weight is less than 10000 Da analyzed by HPLC spectrum (shown in FIG. 1), preferably between 2000-8000 Da.

TABLE 1

Influence on activity of cardio myopeptidin at different pH and different time period (MTT method) ($x \pm s$, n = 8)

| Group | Activity of cardio myopeptidin OD value ($x \pm s$) | |
| --- | --- | --- |
| | 30 μg/ml | 5 μg/ml |
| Normal control group | 0.691 ± 0.032** | |
| Adriamycin group | 0.274 ± 0.011 | |
| Different pH group | | |
| 3.0 | | |
| 30 min | 0.331 ± 0.014** | 0.320 ± 0.015** |
| 60 min | 0.314 ± 0.007** | 0.309 ± 0.010** |

TABLE 1-continued

Influence on activity of cardio myopeptidin at different pH and different time period
(MTT method) (x ± s, n = 8)
Activity of cardio myopeptidin OD value (x ± s)

| Group | | 30 μg/ml | 5 μg/ml |
|---|---|---|---|
| 4.0 | 30 min | 0.315 ± 0.008** | 0.307 ± 0.015** |
|  | 60 min | 0.334 ± 0.015** | 0.311 ± 0.007** |
| 5.0 | 30 min | 0.364 ± 0.022** | 0.379 ± 0.019** |
|  | 60 min | 0.364 ± 0.017** | 0.353 ± 0.023** |
| 6.0 | 30 min | 0.341 ± 0.023** | 0.344 ± 0.011** |
|  | 60 min | 0.332 ± 0.015** | 0.327 ± 0.016** |
| 7.0 | 30 min | 0.320 ± 0.018** | 0.358 ± 0.023** |
|  | 60 min | 0.327 ± 0.010** | 0.328 ± 0.012** |
| 8.0 | 30 min | 0.339 ± 0.008** | 0.332 ± 0.022** |
|  | 60 min | 0.308 ± 0.015 | 0.309 ± 0.010 |
| 9.0 | 30 min | 0.313 ± 0.006** | 0.289 ± 0.020 |
|  | 60 min | 0.279 ± 0.017 | 0.274 ± 0.013 |

**Comparing with Damage Group P < 0.01

It can be seen from Table 1 that the biological activity of cardio myopeptidin is stable at pH 3~8.

Figure 3:
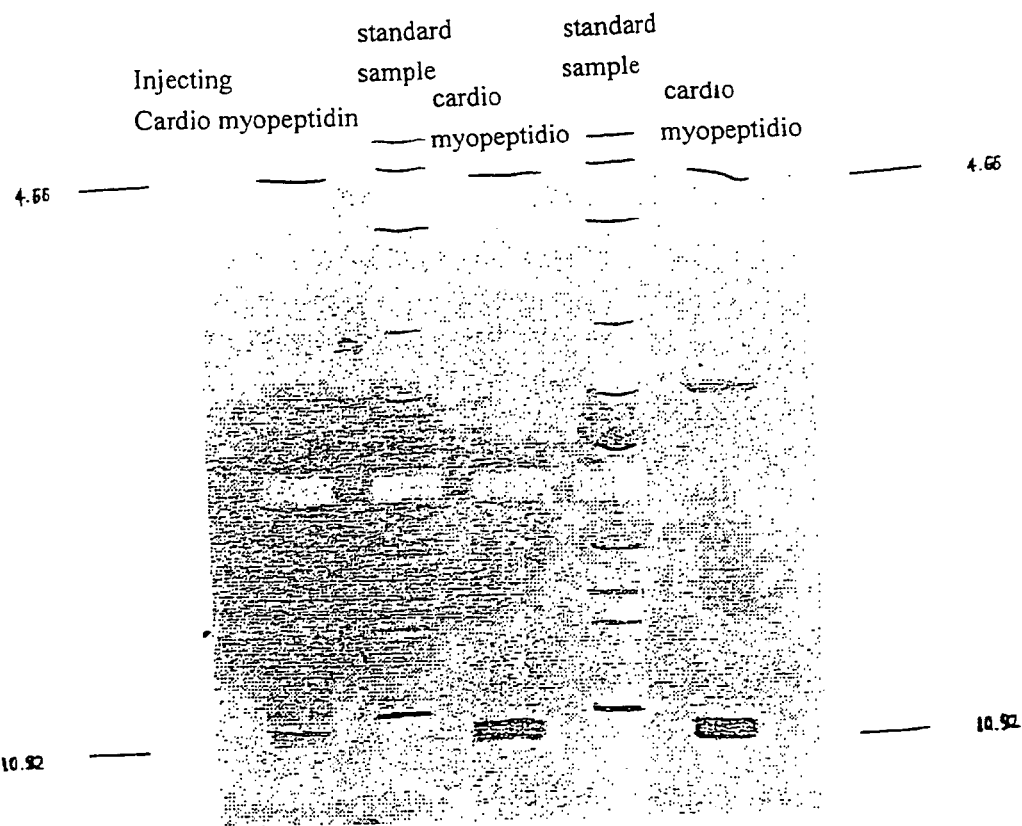
FIG. 3 is an isoelectrofocusing electrophoresis spectrum of cardio myopeptidin of the present invention.

The cardio myopeptidin of this invention principally showed five peaks on FPLC analysis, and the sum of relative area is 90%~95%. It is indicated by activity test that the five peaks can all promote the activity of succinic dehydrogenase of primarily cultured myocardial cells and the myocardial cells with oxygen re-supplied due to lack of oxygen (Table 2), among which the activity of peak P1 is comparatively high. Polypeptide content in cardio myopeptidin is 75-90☐, free amino acids content is 6-15☐, and there is a little nucleic acid and microelement. Isoelectrofocusing electrophoresis of cardio myopeptidin displays two stained bands, among which the band of pI 10.92 is the one with deeper color (shown in FIG. 3).

TABLE 2

Influence of each peak of cardio myopeptidin on enzyme activity of myocardial cells (MTT method) (n = 8, $\bar{x}$ ± s)

| Group | OD value ($\bar{x}$ ± s) 5 μg/ml | t |
|---|---|---|
| Normal control group | 0.344 ± 0.014** | 9.93 |
| Adriamycin group | 0.272 ± 0.015 |  |
| P1 | 0.318 ± 0.004** | 6.344 |
| P2 | 0.295 ± 0.012** | 3.39 |
| P3 | 0.309 ± 0.012** | 5.45 |
| P4 | 0.317 ± 0.017** | 5.61 |
| P5 | 0.303 ± 0.014** | 4.27 |
| Cardio myopeptidin | 0.298 ± 0.005** | 3.47 |

Note:
Compared with Adriamycin group, **P < 0.01

It can be seen from Table 2 that all five component peaks can promote the activity of succinic dehydrogenase of primarily cultured myocardial cells.

1.1. Identification of Polypeptide 1 ml of cardio myopeptidin solution with the concentration of 2.5 mg/ml is dissolved with 2 ml of water, in which 2 ml of biuret reagent is added and mixed well. [Preparation of biuret reagent: 0.75 g of copper sulphate ($CuSO_4.5H_2O$) and 3 g of potassium sodium tartrate ($NaKC_4H_4O_6.4H_2O$) is dissolved with 250 ml of water, to which 150 ml of 10% sodium hydroxide is added while stirring and diluted with water to 500 ml, then store the solution in a plastic bottle.] If the solution contains polypeptide, a royal purple solution will be produced. After testing samples from 6 batches, cardio myopeptidin of this invention showed royal purple, which indicates that cardio myopeptidin of this invention contains polypeptide.

1.2 Assay (1) Semi-micro Kjeldahl Method for the Determination of Nitrogen

Test sample: cardio myopeptidin solution & cardio myopeptidin for injection.

Cardio myopeptidin solution with the Batch No. 960419, 960422 and 960423; cardio myopeptidin for injection with the Batch No. 960501, 960502 and 960503 is dissolved with water to required concentration before testing.

Reagents: sulfuric acid: chemically pure and specific gravity is 1.84; digestion reagent: mixture of 1 unit of copper sulphate ($CuSO_4.5H_2O$) and 10 units of potassium sulphate ($K_2SO_4$) ground into fine particles; 12.5 mol/L of sodium hydroxide solution; 2% boric acid absorption solution; 10% sodium tungstate; 0.33 mmol/L of sulfuric acid; mixed indicator: mixture of 5 units of 0.2% (w/v) bromcresol green alcoholic solution and 2 units of 0.1% (w/v) methyl red alcoholic solution; and 0.01 mol/L hydrochloric acid.

Calculation formula:

Total nitrogen content in test sample product (g/L)=
(Titration volume of sample–titration of blank)×
conc of standardized hydrochloric acid Volume
of sample (ml)

Determination: Proceed as directed under *Determination of Nitrogen* (see Method 2, Appendix VII D, Volume II of CHINA PHARMACOPOEIA, refer to CP hereinafter, 1995).

Inorganic nitrogen: 5 ml of sample is measured accurately, to which 3 ml of water, 1 ml of 10% sodium tungstate, and 0.33 mmol/L sulfuric acid are added and mixed well. The mixture solution is filtered after standing for 30 minutes. 5 ml of the filtrate and 5 ml of sodium hydroxide test solution are transferred accurately to a distillation flask, and the test proceeds as directed under the above-mentioned *Determination of Total Nitrogen*.

Total nitrogen: a vial of cardio myopeptidin for injection is dissolved in 4 ml of water, then 2.0 ml of the injection solution is measured accurately, while 2.0 ml of cardio myopeptidin solution is measured accurately, and the test proceeds separately as directed under the above-mentioned Determination of Total Nitrogen.

Organic nitrogen=Total nitrogen–inorganic nitrogen

Note: (1) During determination of inorganic nitrogen, because foam may easily be produced in the distillation process, which will lead sodium hydroxide being taken into the condenser tube and subsequently flow into the collected liquid, the determination result will be an upper bound to the true value. Therefore, 10% sodium tungstate and 0.33 mmol/L sulfuric acid are added before distillation to remove organic substances, then inorganic nitrogen is determined by the filtrate.

(2) The main components of the test sample (cardio myopeptidin) are polypeptide substances. Inorganic compound used in the manufacturing process may produce inorganic nitrogen and affect the determination result. After determining the content of total nitrogen by this method, the content of inorganic nitrogen in the test sample is determined, and the difference of the total nitrogen content minus inorganic nitrogen content gives the organic nitrogen content of the present invention.

Results & Analysis

Nitrogen content of cardio myopeptidin solution and cardio myopeptidin for injection with different batch numbers is shown in Table.

TABLE 3

Measurement results of nitrogen content in test samples with different batch numbers

| | Cardio myopeptidin solution (mgN/ml) | | | Cardio myopeptidin for injection (mgN/vial) | | |
|---|---|---|---|---|---|---|
| | Batch No. | | | | | |
| | 960419 | 960422 | 960423 | 960501 | 960502 | 960503 |
| Total N | 1.788 | 1.926 | 1.628 | 3.816 | 4.250 | 4.100 |
| Organic N | 1.589 | 1.743 | 1.460 | 3.612 | 3.919 | 3.722 |
| Inorganic N | 0.199 | 0.183 | 0.168 | 0.204 | 0.331 | 0.378 |

Table 3 shows that the organic nitrogen content of cardio myopeptidin solution is 1.46-1.74 mg/ml, and that of cardio myopeptidin for injection is 3.61-3.92 mg/vial, and the average content is 1.60 mg nitrogen/ml and 3.75 mg nitrogen/vial, respectively.

(2) Folin-phenol Reagent Method

Cardio myopeptidin solution with the Batch No. of 960419, 960422 and 960423; Cardio myopeptidin for injection (CMI) with the batch No of 960501, 960502 and 960503, dissolved with water to proper concentrations before measurement; Reference substance: Bovine serum albumin with Batch No. 9607 (provided by the National Institute for the Control of Pharmaceutical and Biological Products).

Apparatus: Model 7221 spectrophotometer, Shanghai.

Preparation of reagents:

4% sodium carbonate solution: 4 g of sodium carbonate ($Na_2CO_3 \cdot 10H_2O$) in 100 ml of water.

0.2 mol/L sodium hydroxide solution: 0.8 g of sodium hydroxide (NaOH) in 100 ml of water.

1% copper sulphate solution: 1 g of copper sulphate ($CuSO_4 \cdot 5H_2O$) in 100 ml of water.

2% potassium tartrate solution: 2 g of potassium tartrate ($K_2C_4H_4O_6 \cdot \frac{1}{2}H_2O$) in 100 ml of water.

Alkaline copper test solution: Take 25 ml each of test solution 1 and 2, and 0.5 ml each of test solution 3 and 4, then mix well.

Phenol Reagent: 100 mg of sodium tungstate ($Na_2WO_4 \cdot 2H_2O$) and 25 g of sodium molybdate ($Na_2MoO_4 \cdot 2H_2O$) are put into a 1500 ml flask, to which 700 ml of water, 50 ml of 85% phosphoric acid and 100 ml of hydrochloric acid are added. A return tube (with cork plug or rubber stopper covered with tin foil) is connected at the top of the flask for boiling and the solution is refluxed in the flask for 10 minutes. Then, the condenser tube is taken off, 150 g of lithium sulfate ($Li_2SO_4$), 50 ml of water and several drops of bromine solution are added into the flask and mixed well. The solution is boiled for 15 minutes in the ventilation hood to remove excess bromine. The solution is cooled down to room temperature, and diluted by the water to 1000 ml, and then filtered to obtain the filtrate, which is stored in a brown bottle in a refrigerator, called stock solution. Dilute the stock solution with water before measurement.

Plotting of Standard Curve

Preparation of the reference solution: Add 100 mg (accurately weighed) of dried bovine serum albumin reference substance (provided by the National Institute for the Control of Pharmaceutical and Biological Products) into a 100 ml volumetric flask, to which water is added to dilute to scale, and mix well. Add accurately 10.0 ml of the dilution to another 10 ml volumetric flask, and dilute with water to scale and mix well.

Preparation for standard curve: 0.0, 0.2, 0.4, 0.6, 0.8 and 1.0 ml of reference solution is added accurately into each of 6 test tubes with stopper and further diluted to 1.0 ml by adding water into each test tube. Then add 5.0 ml of alkaline copper solution to each test tube and mix well, and place the test tube at room temperature for 10 minutes. Then rapidly add 0.5 ml phenol reagent to each test tube and mix well immediately. Stand the test tube in a water bath (35° C.) for 30 minutes. Remove and cool the test tube to room temperature. Take the test tube with 0.0 ml of reference solution as blank, and determine the absorbance at 660 nm wavelength as directed under spectrophotography (Appendix IV A, Volume II, of CHINA PHARMACOPOEIA 1995). Plot a standard curve by using the absorbance as ordinate and the protein concentration as horizontal coordinate (absorbance vs mg protein).

Determination method: Dissolve and dilute a certain amount of test sample of cardio myopeptidin with water, and add an accurately measured volume of the solution or the dilution to a 50 ml volumetric flask, add water to scale and mix well. Then accurately pipette 10.0 ml mixture to a 50 ml volumetric flask, add water to scale and mix well, and exactly pipette 1.0 ml to a test tube with stopper. After that, proceed with the measurement procedure according to above-mentioned "Preparation for Standard Curve" from 'to add alkaline copper solution . . . ' until the determination of absorbance as directed. Check and obtain corresponding concentration from the standard curve, and then calculate.

Result & Analysis

The determination result is shown in Table 4.

It is shown from the determination result that the polypeptide concentration of cardio myopeptidin solution is 2.6-2.8 mg per ml, and the content of cardio myopeptidin for injection is 9.2-9.9 mg per vial. In order to keep the content of polypeptide in the solution and in the injection vial constant, we specify that the concentration of polypeptide in cardio myopeptidin solution is more than 2.5 mg/ml, and that in cardio myopeptidin for injection, it is 9.0-11.0 mg/vial.

TABLE 4

Comparison among the determination results of three peptide determination methods
Peptide determination methods

|  | Biuret reagent* | Folin-phenol reagent | Semi-micro Kjeldahl |
|---|---|---|---|
|  | CMS** (mg/ml) | | |
| 960419 | 1.65 | 2.7 | 1.58 |
| 960422 | 1.85 | 2.8 | 1.74 |
| 960423 | 2.00 | 2.6 | 1.46 |
|  | CMI** (mg/vial) | | |
| 960501 | 3.26 | 9.9 | 3.61 |
| 960502 | 3.63 | 9.2 | 3.92 |
| 960503 | 3.73 | 9.2 | 3.72 |

Note:
*Biuret reagent method is determined with a fully automatic biochemistry analyzer.
**CMS: cardio myopeptidin solution; CMI: cardio myopeptidin for injection It can be seen from Table 4 that three peptide determination methods lead to inconsistent results. The reaction principle of the Folin-phenol reagent method lies in the reactivity of phenolic group of aromatic amino acids, which have good specificity and is easy to be manipulate. The use of specific reference substance and the plotting of standard curve in each determination can overcome nonlinear relationship. Thus, Folin-phenol reagent method is taken to determine the content of polypeptide in cardio myopeptidin solution and cardio myopeptidin for injection.

(3) Analysis of Composition of Cardio Myopeptidin

The cardio myopeptidin of the present invention mainly comprises polypeptides; the organic nitrogen contents of polypeptides and free amino acids are determined separately. The organic nitrogen content of polypeptide is the difference when the organic nitrogen content of free amino acid is subtracted from the total organic nitrogen content; that is, the organic nitrogen content of polypeptide=total organic nitrogen content−the organic nitrogen content of free amino acid.

Reagents and methods are the same as described above (please read the method for the determination of nitrogen).

Result: Table 5 shows the nitrogen content of free amino acids in three batches of cardio myopeptidin for injection.

TABLE 5

Nitrogen content of free amino acids in cardio myopeptidin for injection
Cardio myopeptidin for injection

|  |  | Batch No. | | |
|---|---|---|---|---|
|  |  | 960501 | 960502 | 960503 |
| Organic nitrogen content of free amino acids | g/L | 0.257 | 0.285 | 0.286 |

The comparisons between organic nitrogen content of cardio myopeptidin for injection and nitrogen content of free amino acids are shown in Table 6.

TABLE 6

Comparison between the total nitrogen content and nitrogen content in free amino acid
Cardio myopeptidin for injection

|  |  | Batch No. | | |
|---|---|---|---|---|
|  |  | 960501 | 960502 | 960503 |
| organic nitrogen contents of polypeptides | g/L | 3.612 | 3.919 | 3.722 |
| organic nitrogen content of free amino acids | g/L | 0.257 | 0.285 | 0.286 |
| nitrogen content of free amino acids/total organic nitrogen content | % | 6.643 | 6.823 | 7.135 |

From Tables 5 and 6, we can see that the nitrogen content of free amino acids in cardio myopeptidin for injection accounts for 6.643%-7.135% of the nitrogen content of the test sample, which shows that polypeptide in the test sample accounts for the majority of the nitrogen content. Considering that the polypeptide of this invention is the major component with biological activity and to make the manufacturing process to be stable and controllable, we specify that the percent composition of polypeptide in cardio myopeptidin for injection is in the range from 75% to 90%.

1.3 Analysis of Ultraviolet Scanning

Use a Model 2201 ultroviolet spectrophotometer produced by Japanese Shimadzu, and proceed as directed under *Spectrophotography* (Appendix IV A, Volume II of CHINA PHARMACOPOEIA 1995).

Figure 4:
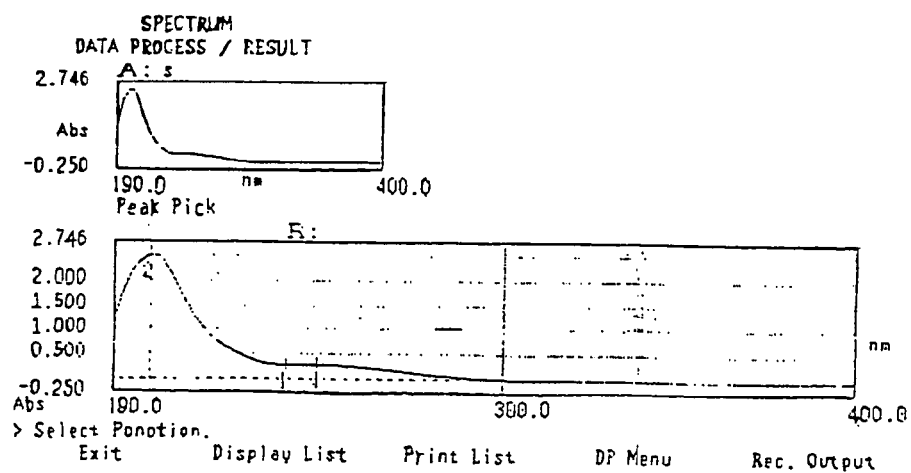
FIG. 4 is a UV spectrum of cardio myopeptidin of the present invention.

The result shows that the maximum absorption peak of cardio myopeptidin solution is at 199.8-201.2 nm, and the maximum peak of cardio myopeptidin for injection is at 200.4-201.8 nm (FIG. 4), which indicates that the ultraviolet spectra of the three batches of solution and three batches of injection are consistent, the major component of the sample is polypeptide, and the manufacturing process of cardio myopeptidin is stable.

TABLE 7

Ultraviolet absorption wavelength of cardio myopeptidin

| Batch No. | Absorption wavelength (nm) |
|---|---|
| cardio myopeptidin solution (mg/ml) | |
| 960422 | 200.4 |
| 960423 | 199.8 |
| 960419 | 201.2 |
| cardio myopeptidin for injection (mg/vial) | |
| 960501 | 200.4 |
| 960502 | 201.8 |
| 960503 | 201.6 |

1.4 Identification of Protein

The test solution does not become turbid when 1 ml of 20% sulfosalicylic acid solution is added to 2 ml of cardio myopeptidin solution with the concentration of 2.5 mg/ml of cardio myopeptidin of this invention, and the determination results of three batches of test sample of cardio myopeptidin for solution and injection indicate that no protein is contained therein. Determining protein by the sulfosalicylic-acid test can not only monitor protein absence in the test sample mixed in, but also can demonstrate that the royal purple displayed by the biuret reagent is polypeptide, not any other substance.

1.5 Molecular Weight and Detection of Peptide Chromatogram

Molecular weight is determined by the HPLC method with an HP1050 liquid chromatograph.

Chromatographic conditions: mobile phase:sodium sulfate (0.1 mol/L)-sodium dihydrogen phosphate (0.05 mol/L)-sodium azide (0.05%), adjust pH to 6.8 by NaOH; flow rate: 0.35 ml/min; column: TOSOH TSK G2000 sw 7.5 mm×300 mm; column temperature: 5° C.; detection wavelength: 280 nm; sample size: 10 μl.

Reference solutions: add mobile phase to a suitable amount each of cytochrome C (MW=12400), aprotinin (MW=6700) and Vitamin $B_{12}$ (MW=1355) respectively to prepare reference solutions with proper concentrations.

Test sample solution: add mobile phase to a bottle of cardio myopeptidin for injection that contains 10 mg of polypeptide to get a test sample solution with the concentration of 5 mg/ml.

Inject the reference solution and the test sample solution into the chromatograph according to the chromatographic conditions, and determine the retention time of each solution. The regression equation of the reference substance is obtained by the least square method with the correlation coefficient not less than 0.99. Plot the standard curve and calculate the molecular weight of the sample from the following formula.

IgMW=A+BtR

IgMW=6.8405−0.1219tRγ=−0.9990

Where MW is the molecular weight, A is a constant, B is the slope, and tR is the retention time (minutes).

Tables 5 and 6 show the results.

TABLE 8

Retention time of the relative area percentage of chromatographic peaks of cardio myopeptidin for injection.

| | Retention time of Chromatographic Peak (min) | | | | |
|---|---|---|---|---|---|
| Batch No. | P1 | P2 | P3 | P4 | P5 |
| 960501 | 30.5 | 31.8 | 32.8 | 35.0 | 38.7 |
| 960502 | 30.5 | 31.2 | 32.8 | 35.0 | 38.7 |
| 960503 | 31.2 | | 32.7 | 35.0 | 38.7 |
| X | 30.7 | 31.5 | 32.7 | 35.0 | 38.7 |

TABLE 9

Molecular weight at peak position of cardio myopeptidin for injection

| | MW (Da) | | | | |
|---|---|---|---|---|---|
| Batch No. | P1 | P2 | P3 | P4 | P5 |
| 960501 | 6023 | 4588 | 3665 | 2233 | 969 |
| 960502 | 6027 | 5261 | 3688 | 2234 | 971 |
| 960503 | 5165 | 3709 | | 2236 | 875 |
| X | 5736 | 4519 | 3676 | 2234 | 971 |

Figure 1:
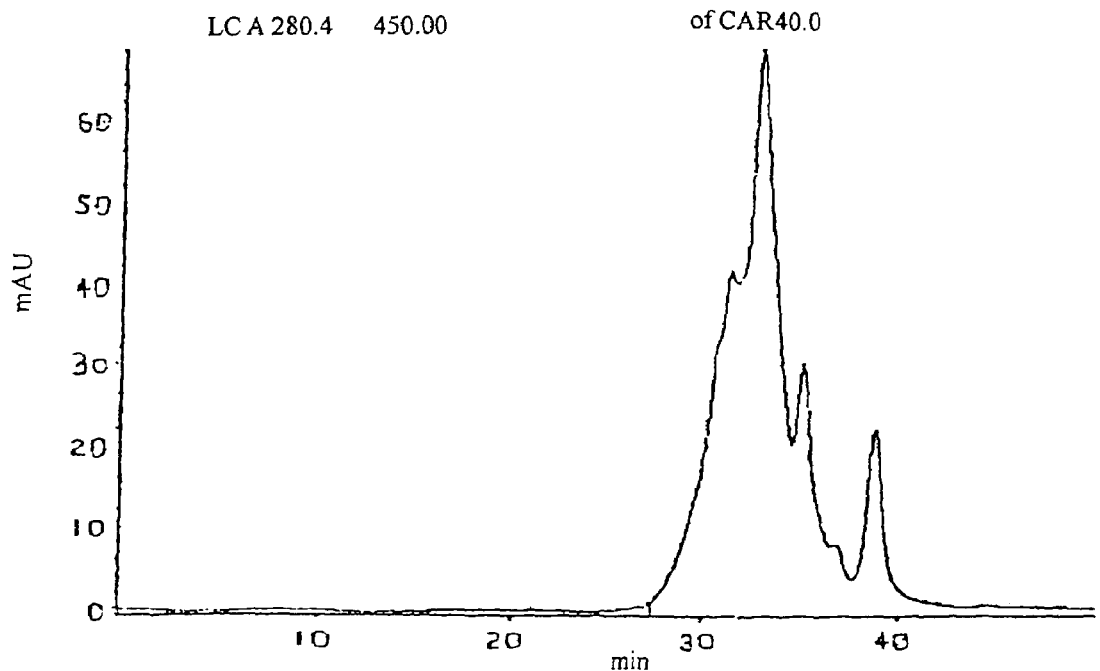
FIG. 1 is an HPLC spectrum of molecular weight of cardio myopeptidin of the present invention.
Figure 2:
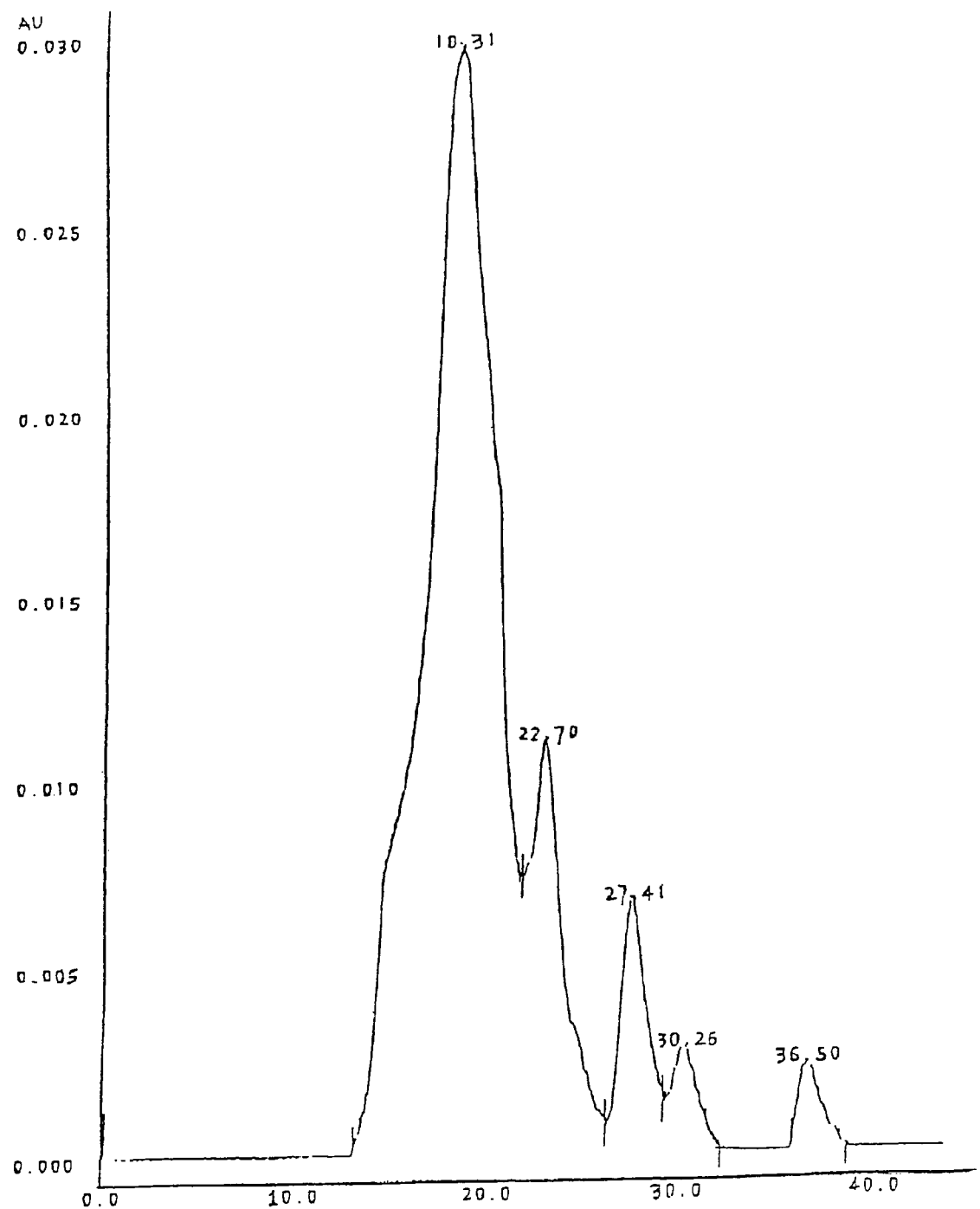
FIG. 2 is a FPLC spectrum of separating and purifying cardio myopeptidin of the present invention.

The molecular weight of cardio myopeptidin for injection ranges from 922 to 6027 Da. The maximum molecular weight ranges from 5214 to 6027 Da (as shown in FIG. 1). That means the test sample is a polypeptide with a small molecular weight, and its molecular weight is less than 10000 Da,. Therefore anaphylactic response will seldom occur when being injected or taken.

1.6 Nucleic Acid 4 ml of distilled water is added to dissolve a bottle of cardio myopeptidin for injection that contains 10 mg of polypeptide. An equal volume of 10 mol/L phenol is added for extracting nucleic acid, then the content of DNA is determined in the supernate. Add two volumes of cold absolute ethyl alcohol and ½₀ volume of 10 mol/L ammonium acetate to the supernate and put it at −80° C. for 30 minutes. Centrifuge at 12000 rpm×20 min, then discard the supernate, and dissolve the precipitate in 4 ml of distilled water. The dissolved precipitate is the sample to determine the RNA content.

(1) Determination of RNA Content

Preparation for standard curve: take 6 test tubes and add in reagents according to following table.

| | added amount (ml) | | | | | |
|---|---|---|---|---|---|---|
| | Test tube No. | | | | | |
| Added substance | 0 | 1 | 2 | 3 | 4 | 5 |
| RNA standard solution | 0 | 0.2 | 0.4 | 0.6 | 0.8 | 1.0 |
| Distilled water | 1.0 | 0.8 | 0.6 | 0.4 | 0.2 | 0 |
| Orcinol reagent | 3.0 | 3.0 | 3.0 | 3.0 | 3.0 | 3.0 |

Mix each tube well and heat in a boiling water bath for 20 min., then take out and cool down to room temperature with cold water. The absorbance of each tube is determined by a spectrophotometer at 670 nm wavelength, adjusting the zero position of absorbance with the No. "0" tube. Plot a standard curve by using RNA content as the abscissa, and the absorbance as the ordinate.

(1) Determination of RNA Content in the Test Sample:

Mark 4 test tubes respectively with "blank tube" and "sample tube." Add 1.0 ml of distilled water to the blank tubes, and 1.0 ml of RNA sample solution to the sample tubes. Add 3.0 ml orcinol reagent in each tube and mix well, then put them in a boiling water bath for 20 minutes. Take out the tubes and cool down to room temperature in a cold bath. The absorbance of each test tube is determined in a spectrophotometer at 670 nm wavelength, adjusting the zero position of absorbance with the blank tube. Finally, RNA content can be obtained by comparing with the standard curve and taking the average value.

(2) Determination of DNA Content

Preparation for standard curve: take 6 test tubes and add in reagents according to the following Table.

| | Added amount ml | | | | | |
|---|---|---|---|---|---|---|
| | Test tube No. | | | | | |
| Added substance | 0 | 1 | 2 | 3 | 4 | 5 |
| DNA standard solution | 0 | 0.2 | 0.4 | 0.6 | 0.8 | 1.0 |
| $DH_2O$ | 1.0 | 0.8 | 0.6 | 0.4 | 0.2 | 0 |
| Diphenylamine reagent | 3.0 | 3.0 | 3.0 | 3.0 | 3.0 | 3.0 |

Mix each tube and heat in a water bath at 60° C. for 60 min, then take out and cool down to room temperature in cold water. The absorbance of each tube is determined by a spectrophotometer at 595 nm wavelength, adjusting the zero position of absorbance with the No. "0" tube. Plot a standard curve by using DNA content as the abscissa, and the absorbance as the ordinate.

Determination of DNA Content in the Test Sample:

Mark 3 test tubes respectively with "blank tube" and "sample tube." Add 1.0 ml of distilled water to the blank tube, and 1.0 ml of DNA sample solution in sample tubes, then add 3.0 ml diphenylamine reagent in each tube and mix well. Put into a water bath at 60° C. for 60 minutes, then take out the tubes and cool down to room temperature in a cold bath. The absorbance of each tube is determined in a spectrophotometer at 595 nm wavelength, adjusting the zero position of absorbance with the blank tube. DNA content can be obtained by comparing with the standard curve and taking the average value.

The results shows that each bottle of cardio myopeptidin for injection contains less than 200 μg (2%) RNA, and the DNA content does not exceed 750 μg (7.5%).

1.7 Activity

Test sample: cardio myopeptidin for injection respectively with the batch number 960501, 960502, 960503, and 960101, and polypeptide content is 10 mg/vial.

Method of primary myocardial cell culture is taken to determine the activity of the present invention. Experimental results are shown in Table 10.

TABLE 10

| t value of activity of cardio myopeptidin for injection (n = 6) | |
|---|---|
| Batch No. | t value |
| 960501 | 5.8 |
| 960502 | 3.2 |
| 960503 | 7.9 |
| 960101 | 7.8 |

1.8 Identification of Cardio Myopeptidin for Injection by HPLC Method

Apparatus: HP1100, module liquid chromatograph No DE 70300954;

Chromatographic condition: Mobile phase: methanol:water=10:90;

Column: ymc-park ODS-A A-302 150 mm×4.6 mm☐I.D S-5 μm 120A No 041543847 (W);

Column temperature: 26° C., detecting wavelength: 254 nm, flow rate: 0.8 ml/min, and sample size: 10 μl.

Determination procedure: Add 10 ml of mobile phase to each bottle of the test sample, and the completely dissolved solution is used for the test.

Batch numbers of test sample of cardio myopeptidin for injection are 960101, 960501, 960502, 960503, 961101, 961103, 971201 and 980301, respectively.

Figure 5:
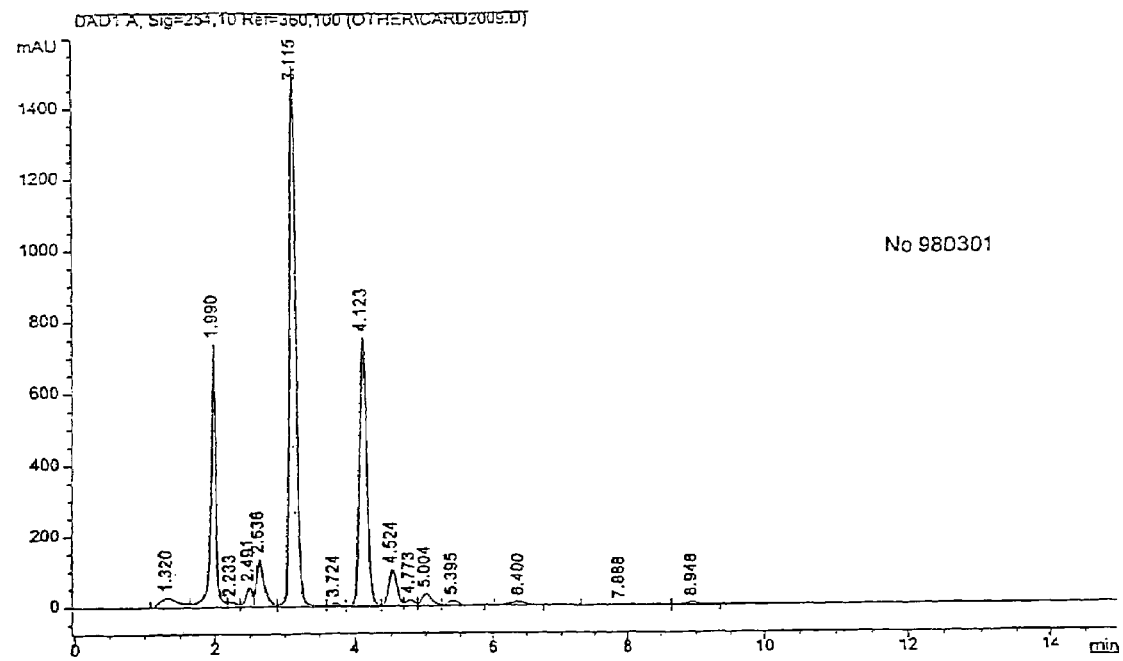
FIG. 5 is an HPLC spectrum for identification of the cardio myopeptidin for injection of the present invention.
Figure 6:
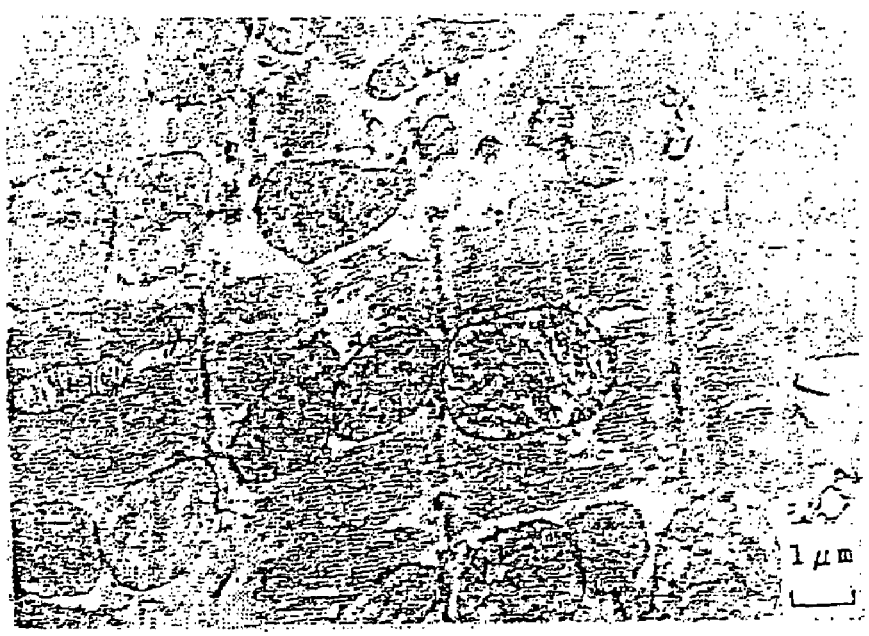
FIG. 6 is a photograph of electron microscope for pseudo-operation control group in the experiment of influence of cardio myopeptidin on damage of myocardial ultrastructure caused by ischemia-reperfusion of the present invention.
Figure 7:
FIG. 7 is a photograph of electron microscope for normal saline reference group in the experiment of influence of cardio myopeptidin on damage of myocardial ultrastructure caused by ischemia-reperfusion of the present invention.
Figure 8:
FIG. 8 is a photograph of electron microscope for ischemia-reperfusion reference group in the experiment of influence of cardio myopeptidin on damage of myocardial ultrastructure caused by ischemia-reperfusion of the present invention.
Figure 9:
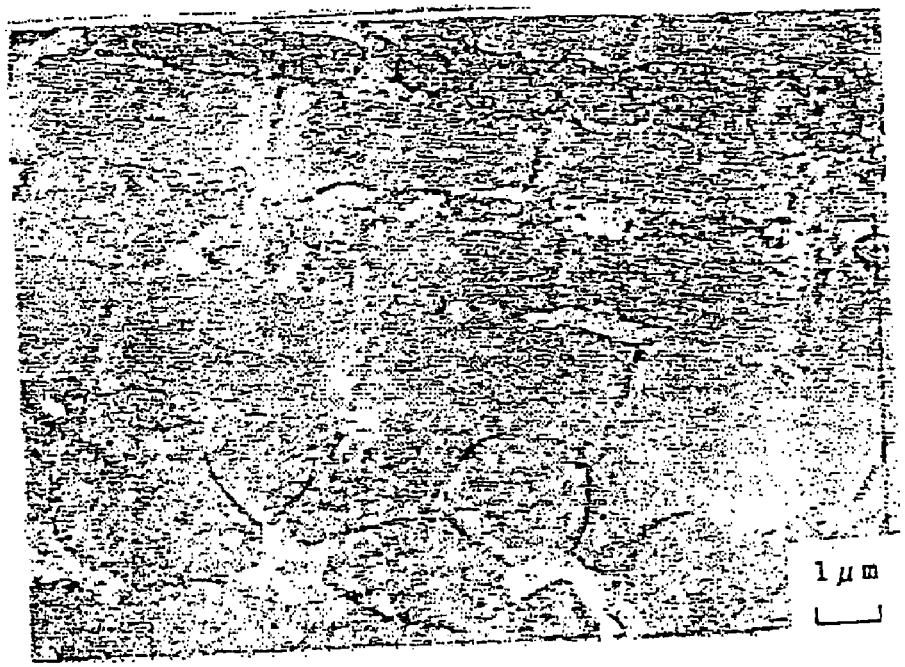
FIG. 9 is a photograph of electron microscope for 10.0 mg/Kg cardio myopeptidin group in the experiment of influence of cardio myopeptidin on damage of myocardial ultrastructure caused by ischemia-reperfusion of the present invention.
Figure 10:
FIG. 10 is a photograph of electron microscope of FIG. 9 for 5.0 mg/kg cardio myopeptidin group.
Figure 11:
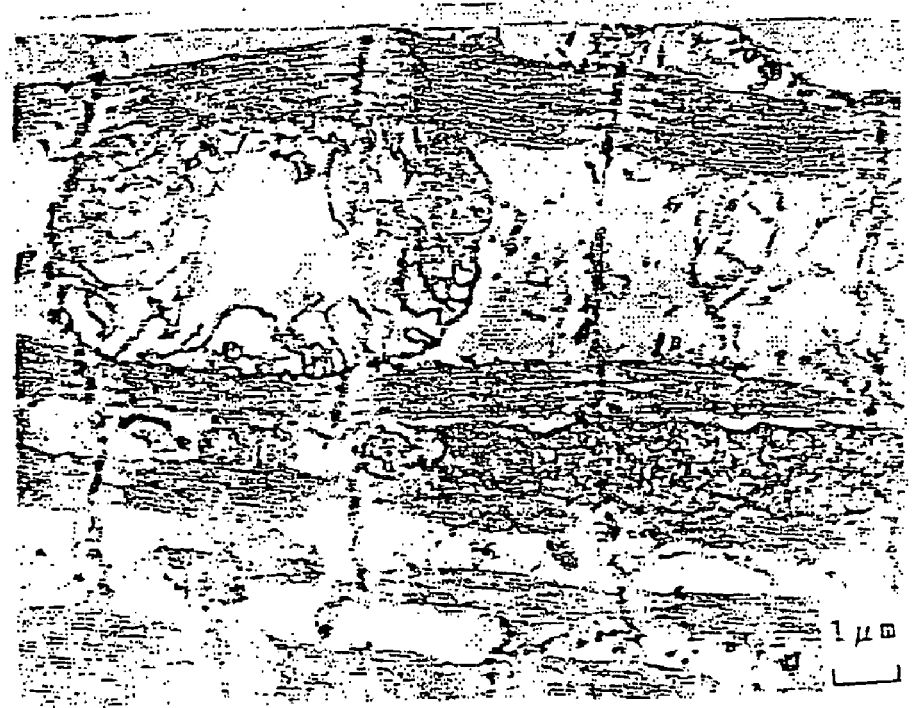
FIG. 11 is a photograph of electron microscope of FIG. 9 for 1.0 mg/kg cardio myopeptidin group.
Figure 12:
FIG. 12 is a photograph of electron microscope of FIG. 9 for 2.0 mg/kg propranolol group.
Figure 13:
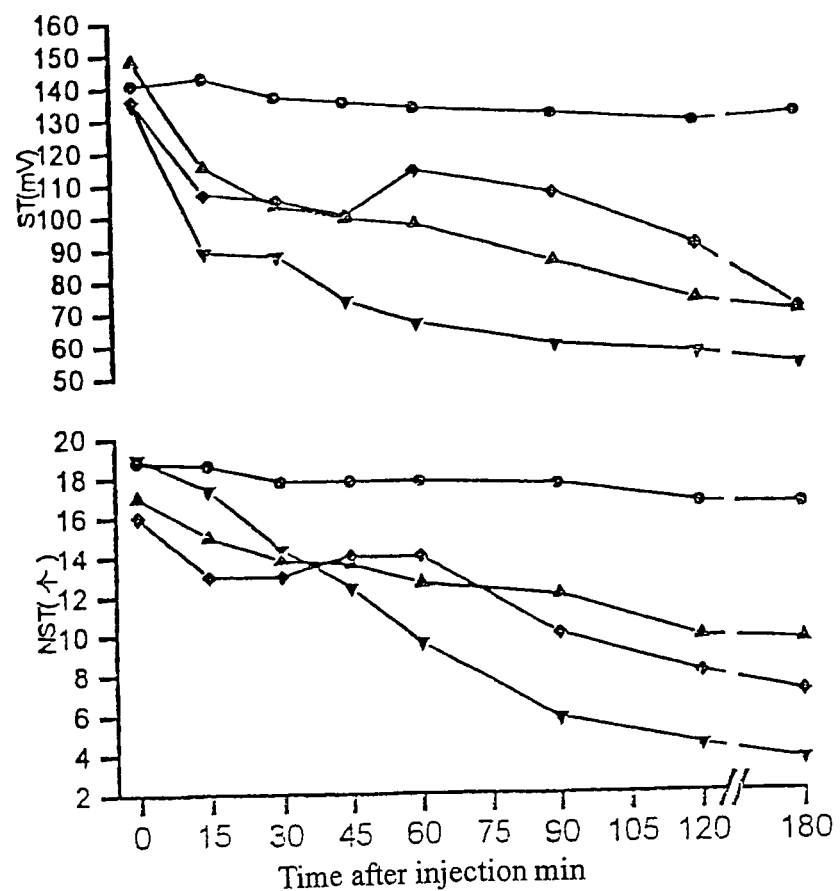
FIG. 13 is a diagram illustrating ST and/or NST in the electrocardiogram of pigs with myocardial infarction being significantly reduced by administered cardio myopeptidin at a dose of 5 mg/kg or 10 mg/kg of body weight.
Figure 14:
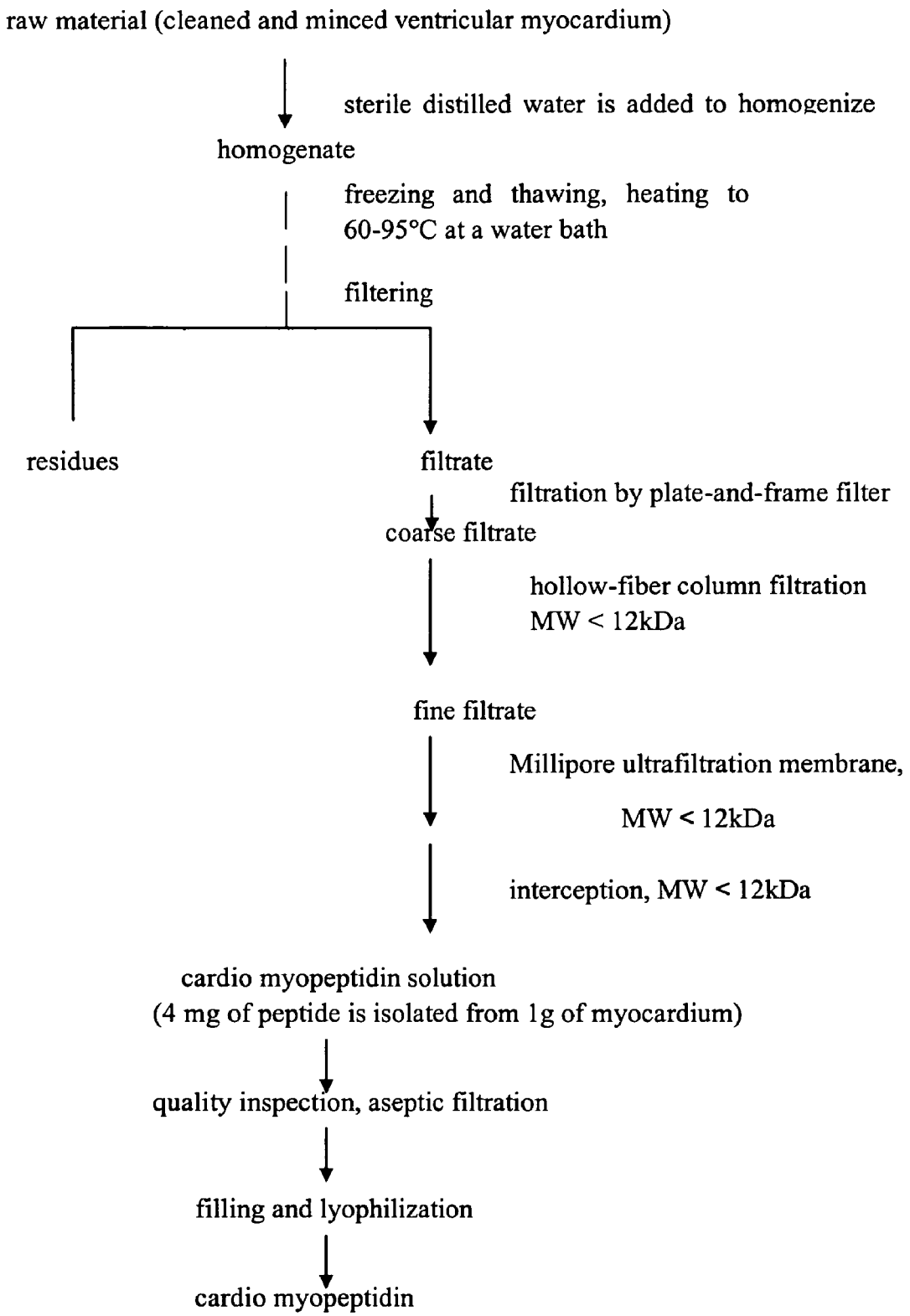
FIG. 14 is a flow chart for explaining the procedure for preparation of cardio myopeptidin of the present invention.

The result shows that the 10 batches of test samples mainly display 4~5 principal peaks, and the relative peak area is more than 85%. The retention time of each principal peak is similar (shown in FIG. 5 and Tables 11 and 12).

TABLE 11

| Retention time of various principal peaks Retention time (min) | | | | | | | | | |
|---|---|---|---|---|---|---|---|---|---|
| Peak | 101 | 501 | 502 | 503 | 1101 | 1102 | 1103 | 201 | 301 |
| P1 | 1.922 | 1.901 | 1.920 | 1.915 | 1.925 | 1.924 | 1.949 | 1.954 | 1.990 |
| P2 | 2.506 | 2.504 | 2.500 | 2.502 | 2.643 | 2.639 | 2.640 | 2.638 | 2.638 |
| P3 | 2.654 | 2.651 | 2.646 | 2.645 | | | | | |

TABLE 11-continued

| Retention time of various principal peaks Retention time (min) | | | | | | | | | |
|---|---|---|---|---|---|---|---|---|---|
| Peak | 101 | 501 | 502 | 503 | 1101 | 1102 | 1103 | 201 | 301 |
| P4 | 3.156 | 3.144 | 3.134 | 3.128 | 3.124 | 3.114 | 3.117 | 3.115 | 3.115 |
| P5 | 4.240 | 4.203 | 4.181 | 4.159 | 4.148 | 4.128 | 4.133 | 4.129 | 4.107 |

TABLE 12

| Relative peak areas of principal peaks Peak areas % | | | | | | | | | |
|---|---|---|---|---|---|---|---|---|---|
| Peak | 101 | 501 | 502 | 503 | 1101 | 1102 | 1103 | 201 | 301 |
| P1 | 18.3 | 12.3 | 13.4 | 15.7 | 13.4 | 13.5 | 11.4 | 14.4 | 16.1 |
| P2 | 10.6 | 11.7 | 9.2 | 12.4 | 5.2 | 5.2 | 5.1 | 5.8 | 4.7 |
| P3 | 10.4 | 13.3 | 11.1 | 8.8 | | | | | |
| P4 | 37.4 | 45.4 | 47.8 | 38.6 | 43.8 | 43.4 | 47.3 | 46.8 | 42.2 |
| P5 | 13.2 | 8.8 | 9.6 | 15.9 | 22.8 | 22.6 | 22.9 | 18.5 | 23.6 |

After storage at 4° C. for 11 months to 3 years, the samples of cardio myopeptidin of this present invention are analyzed by HPLC according to aforesaid chromatographic conditions. It is shown that the retention times of the test samples of 10 batches are similar to the above result. The discrimination index is the proportion of the relative retention time of principal peaks 1, 4 and 5, therein, the sum of the relative percentage of three peaks area is more than 66%, and the proportion of the relative retention time of principal peaks 1, 4 and 5 is 1:1.61:2.14 (±0.1) through calculation.

EXPERIMENTAL EXAMPLE 2

The main pharmacodynamics study for the cardio myopeptidin of the present invention is conducted. The influence and effect of cardio myopeptidin on myocardial morphological index, physiologic index, biochemical indicators, and myocardial oxygen consumption is studied and observed in vitro and in vivo on the myocardial ischemia and ischemia-reperfusion model. The pharmacodynamics experiment and results are as follows:

1. Influence of Cardio Myopeptidin on Damage of Myocardial Ultrastructure Caused by Ischemia-reperfusion By reference to literature methods, sublingually administer cardio myopeptidin or the reference drug through intravenous injection after rat's coronary artery LAD is ligated for 5 minutes; loosen the ligature after 10 minutes of myocardial ischemia, and reperfusion for 30 min, and simultaneously record II-lead ECG. Blood is taken from the abdominal aorta after the completion of reperfusion, and the heart is perfused and fixed with 6% glutaraldehyde and 0.1 M sodium cacodylate buffer for 2 hours after it is perfused and cleaned with physiological saline water through the aorta. Then the ischemic cardiac muscle from the left frontal wall is picked and cut into 1 mm$^3$ slices. The slices are immersed in 4% glutaraldehyde and 0.1 M sodium cacodylate buffer to be fixed for the preparation of electron microscope specimens. Slice the specimen of each cardiac muscle after fixation with osmic acid, serial dehydration with acetone, embedment and polymerization with epoxy resin 618, and for each cardiac muscle, cut 4 embedded pieces. Randomly take 20 photos for each group of cardiac muscle of animals with the negative magnification equal to 12000. Observe the change in the ultrastructure, and classify and determine the value according to categories of pathologic changes and severity of damage of mitochondrion, myocardial fiber and other components. The experiments are divided into seven groups, respectively pseudo-operation (P-O) control group and three dose groups such as ischemia-reperfusion (I-R) group, ischemia-reperfusion+normal saline group or +propranolol (I-R+N.S,I-R+Pro) group and ischemia-reperfusion+cardio myopeptidin (I-R+MTP) of three differen dosage group.

TABLE 13

Influence of cardio myopeptidin on semi-quantitative histological assay of cardiac muscle of ischemia-reperfusion in rats observed under electron microscope (n = 20, x ± s)

| Group | Dosage mg/Kg | Value of pathological changes ± SD |
|---|---|---|
| Pseudo-operation control | — | 0.36 ± 0.46 |
| Ischemia-reperfusion | — | 1.97 ± 1.4$^{\triangle\triangle\triangle}$ |
| Ischemia-reperfusion + normal saline | — | 2.68 ± 1.3* |
| Ischemia-reperfusion + cardio myopeptidin | 1.0 | 1.85 ± 1.6* |
| | 5.0 | 0.73 ± 0.96*** |
| | 10.0 | 0.33 ± 0.42*** |
| Ischemia-reperfusion + propranolol | 2.0 | 0.71 ± 0.84*** |

Note:
Compared with pseudo-operation control group, $^{\triangle\triangle\triangle}$P < 0.01; compared with ischemia-reperfusion group, *P > 0.05, ***P < 0.01.

It is indicated from the experiments that cardio myopeptidin can obviously lessen the damage of myocardial ultrastructure caused by myocardial ischemia-reperfusion, and make or repair it to approach or return to normal condition (as shown in FIG. 6-12).

2. Influence of Cardio Myopeptidin on Myocardial Ischemia

Refer to the literature method and make certain modification as required. Lay open the pericardium at LAD after cats are incised with the heart exposed. Render acute myocardial ischemia for 10 minutes through compression method with plastic casing, then loosen for 30 minutes. Sew up the cloth containing five groups (each group has three) of electrodes on the pericardium of the ischemic cardiac muscle. Record I, II and III-lead electrocardiograms of each group. Simultaneously record the aortic pressure by femoral arterial cannulas. Take ischemia 1', 4' and 7' and reperfuse 1', 5', 10' and 20' and persistently block 1', 5', 10', 15', 20', 30', 40', 50' and 60' as the time of recording. Take the ST elevation and descent expressed in millivolt to represent the change. Block each cat for 5 times, administer different drugs through intravenous injection five minutes before the fourth block, block the LAD persistently for the fifth time, and administer cardio myopeptidin with different doses through intravenous injection in 20 minutes, 30 minutes and 40 minutes after the block, and administer propranolol in 30 minutes after the completion of persistent block. Respectively record and Σ☐ST and ΣNST of each group at the third, fourth and fifth block. The experiment cats are divided into 6 groups of: ischemia-reperfusion group (I-R); ischemia-reperfusion in combination with normal saline group (I-R+N.S); ischemia-reperfusion in combination with 2.0, 5.0 or 10.0 mg/kg of cardio myopeptidin groups (I-R+MTP 2.0, 5.0 or 10.0 mg/kg) and ischemia-reperfusion in combination with 2.0 mg/kg of propranolol group (I-R+Pro).

TABLE 14

Effect of prophylactic administration of cardio myopeptidin on ΣΔST and ΣNST at ischemia stage of epicardium electrocardiogram of cats (x ± s)

| Group | Dosage mg/Kg | n | ΣΔST mV | ΣNST Num. |
|---|---|---|---|---|
| Ischemia-reperfusion | — | 10 | 109 ± 32 | 28.9 ± 5.2 |
| Ischemia-reperfusion + normal saline | — | 10 | 115 ± 24* | 31.1 ± 5.1* |
| Ischemia-reperfusion + cardio myopeptidin | 2.0 | 6 | 70.8 ± 16*** | 19.5 ± 4.8*** |
| | 5.0 | 6 | 37.8 ± 12*** | 9.33 ± 3.9*** |

Note:
Compared with ischemia-reperfusion group, *P > 0.05, ***P < 0.01

TABLE 15

Effect of therapeutic administration of cardio myopeptidin on ΣΔST and ΣNST of epicardium electrocardiogram of cats (x ± s)

| Group | Dosage mg/Kg | n | ΣΔST mV | ΣNST Num. |
|---|---|---|---|---|
| Ischemia | — | 12 | 40.5 ± 10 | 11.1 ± 2.1 |
| Ischemia + normal saline | — | 12 | 40.0 ± 12* | 11.2 ± 1.5* |
| Ischemia + cardio myopeptidin | 2.0 | 6 | 29.9 ± 2.9*** | 8.67 ± 2.2** |
| | 5.0 | 6 | 25.6 ± 5.7*** | 7.33 ± 1.5*** |
| | 10.0 | 6 | 19.7 ± 4.0*** | 6.17 ± 1.2*** |
| Ischemia + propranolol | 2.0 | 6 | 22.8 ± 6.4*** | 6.17 ± 1.5*** |

Note:
Compared with ischemia group, *P > 0.05, P < 0.05, *P < 0.01.

The electrocardiogram of the epicardium shows that cardio myopeptidin can obviously antagonize ST elevation caused by myocardial ischemia in cats and reduce the scope of myocardial ischemia.

3. Effect of Cardio Myopeptidin on Release of Myocardial Creatine Phosphokinase (CPK) Caused by Myocardial Ischemia-reperfusion, Activity of Lactate Dehydrogenase (LDH) and Contents of Free Fatty Acid (FFA) and Malon Dialdehyde (MDA)

(1) Refer to literature methods to make myocardial ischemia-reperfusion damage animal model. Ligate the left anterior descending branch of the coronary artery of rats for 10 minutes after MTP or verapamil (Ver) is sublingually administered through intravenous injection for 5 min, perfuse for 30 min. Continuously observe II-lead ECG through a polygraph. Take 2 ml left heart blood after the completion of reperfusion, and take the cardiac muscle at the cardiac apex of the left ventricle after the heart is perfused through the aorta. Store the cardiac muscle at 4° C. and detect within 48 h. Grouping of the experiment: In the experiment, the rats are divided into seven groups: pseudo-operation control group (P); ischemia-reperfusion group (ischemia-reperfusion, I-R); ischemia-reperfusion+normal saline group (I-R+N.S); ischemia-reperfusion +0.5, 2.0 or 10.0 mg/Kg cardio myopeptidin groups (I-R+MTP) and ischemia-reperfusion +1.0 mg/Kg verapamil group (I-R+Ver), 8-10 animals in each group.

TABLE 16

Effect of prophylactic administration of cardio myopeptidin on activities of cardiac muscle and plasma CPK of rats with ischemia-reperfusion in rats (x ± s)

| Group | Dosage mg/kg | n | Cardiac muscle CPK u/100 mg pro | Plasma CPK u/100 ml |
|---|---|---|---|---|
| Pseudo-operation control | | 10 | 980 ± 63 | 164 ± 64 |
| Ischemia-reperfusion | | 10 | 522 ± 65$^{\triangle\triangle\triangle}$ | 374 ± 54$^{\triangle\triangle\triangle}$ |
| Ischemia-reperfusion + normal saline | | 8 | 501 ± 59* | 337 ± 48* |
| Ischemia-reperfusion + cardio myopeptidin | 0.5 | 8 | 732 ± 98*** | 210 ± 50*** |
| | 2.0 | 8 | 904 ± 95*** | 157 ± 31*** |
| | 10.0 | 8 | 976 ± 95*** | 134 ± 24*** |
| Ischemia-reperfusion + verapamil | 1.0 | 8 | 886 ± 115*** | 192 ± 60*** |
| Ischemia-reperfusion + GMGSP | 5.0 | 8 | 890 ± 97*** | 199 ± 35*** |

Note:
Compared with pseudo-operation control group, $^{\triangle\triangle\triangle}P < 0.01$; compared with ischemia-reperfusion group, *$P > 0.05$, ***$P < 0.01$.

TABLE 17

Effect of prophylactic administration of cardio myopeptidin on activities of cardiac muscle and plasma LDH of rats with ischemia-reperfusion (x ± s)

| Group | Dosage mg/Kg | n | Cardiac muscle LDH u/mg pro | Plasma LDH u/ml |
|---|---|---|---|---|
| Pseudo-operation control | | 10 | 76.7 ± 19 | 40.9 ± 9.5 |
| Ischemia-reperfusion | | 10 | 110 ± 27$^{\triangle\triangle\triangle}$ | 120 ± 20$^{\triangle\triangle\triangle}$ |
| Ischemia-reperfusion + normal saline | | 8 | 112 ± 19* | 116.2 ± 12* |
| Ischemia-reperfusion + cardio myopeptidin | 0.5 | 8 | 97.1 ± 12* | 93.9 ± 17*** |
| | 2.0 | 8 | 76.3 ± 22*** | 59.7 ± 12*** |
| | 10.0 | 8 | 64.8 ± 17*** | 52.6 ± 13*** |
| Ischemia-reperfusion + verapamil | 1.0 | 8 | 75.1 ± 23*** | 46.7 ± 8.8*** |
| Ischemia-reperfusion + GMGSP | 5.0 | 8 | 83.0 ± 17*** | 60.9 ± 15*** |

Note:
Compared with pseudo-operation control group, $^{\triangle\triangle\triangle}P < 0.01$; compared with ischemia-reperfusion group, *$P > 0.05$, ***$P < 0.01$.

TABLE 18

Effect of prophylactic administration of cardio myopeptidin on cardiac muscle and plasma MDA content of rats with ischemia-reperfusion (x ± s)

| Group | Dosage mg/kg | n | Cardiac muscle MDA nmol/100 mg pro | Plasma MDA nmol/ml |
|---|---|---|---|---|
| Pseudo-operation control | | 10 | 68.3 ± 8.4 | 22.3 ± 1.8 |
| Ischemia-reperfusion | | 10 | 135 ± 10$^{\triangle\triangle\triangle}$ | 63.6 ± 11$^{\triangle\triangle\triangle}$ |
| Ischemia-reperfusion + normal saline | | 8 | 127 ± 15* | 58.4 ± 11* |
| Ischemia-reperfusion + cardio myopeptidin | 0.5 | 8 | 73.1 ± 13*** | 38.1 ± 6.2*** |
| | 2.0 | 8 | 60.5 ± 10.4*** | 27.7 ± 5.5*** |
| | 10.0 | 8 | 49.8 ± 9.4*** | 25.5 ± 5.1*** |
| Ischemia-reperfusion + verapamil | 1.0 | 8 | 66.6 ± 19.8*** | 24.9 ± 6.6*** |
| Ischemia-reperfusion + GMGSP | 5.0 | 8 | 75.2 ± 9.7*** | 39.2 ± 5.3*** |

Note:
Compared with pseudo-operation control group, $^{\triangle\triangle\triangle}P < 0.01$; compared with ischemia-reperfusion group, *$P > 0.05$, ***$P < 0.01$.

TABLE 19

Effect of cardio myopeptidin on plasma FFA content of rats with ischemia-reperfusion (n = 8, x ± s)

| Group | Dosage mg/kg | FFA μmol/100 ml |
|---|---|---|
| Pseudo-operation control | — | 60.6 ± 7.8 |
| Ischemia-reperfusion | — | 129 ± 26$^{\triangle\triangle\triangle}$ |
| Ischemia-reperfusion + normal saline | — | 121 ± 10* |
| Ischemia-reperfusion + cardio myopeptidin | 1.0 | 85.4 ± 5.0*** |
| | 5.0 | 77.7 ± 7.1*** |
| | 10.0 | 71.4 ± 11*** |

TABLE 19-continued

Effect of cardio myopeptidin on plasma FFA content of rats with ischemia-reperfusion (n = 8, x ± s)

| Group | Dosage mg/kg | FFA μmol/100 ml |
|---|---|---|
| Ischemia-reperfusion + propranolol | 2.0 | 77.1 ± 6.4*** |
| Ischemia-reperfusion + GMGSP | 5.0 | 89.2 ± 6.7*** |

Note:
Compared with pseudo-operation control group, $^{\triangle\triangle\triangle}P < 0.01$; compared with ischemia-reperfusion group,, $*P > 0.05$, $***P < 0.01$.

Compared with the growth-stimulating peptide of the myocardial cells (GMGSP) disclosed in Chinese patents of ZL94102798 and ZL94102799, cardio myopeptidin of the present invention obviously has higher in vitro biological activity. The biological activity of said cardio myopeptidin is 3~5 times higher than that of the growth-stimulating peptide of the myocardial cells. Comparison data of in vivo results show it poses a favorable impact on the release of myocardial creatine phosphokinase, biological activity of lactate dehydrogenase, and contents of free fatty acid and malon dialdehyde caused by myocardial ischemia-reperfusion injury (as shown in Table 16-19).

(2) Refer to literature methods to make Langendorff's cardiac hypoxia-reoxygenation damage animal model of isolated rat heart. Conduct Langendorff's perfusion with K—H liquid with high Ca2+ and low K+ and persistent filling of mixed gas. Hook two platinum filaments on the apex of heart and the root of the left cardiac atrium respectively, and record the electrocardiogram. Ligate LAD for 10 min and loosen for 15 min. Conduct perfusion with K—H liquid with corresponding concentrations of cardio myopeptidin from 5 min before ligation to 5 min after loosening for the cardio myopeptidin-treated group. Determine the related indexes of effluent before and after 8 min of ligation and 2 min after loosening respectively. Take the cardiac muscles of the frontal and posterior wall of the left ventricle after the completion of perfusion. Store the muscles at 4° C. and detect their CPK, LDH and MDA within 48 h. In the experiment, rats are divided into 6 groups: pseudo-operation control group (P-O), hypoxia-reoxygenation group (anoxia-reoxygenation, A-R), hypoxia-reoxygenation+10, 50 or 100 μg/ml cardio myopeptidin (final concentration, A-R+MTP) groups and hypoxia-reoxygenation+1.0 μg/Kg verapamil (A-R+Ver) group, and each group contains 10 animals.

TABLE 20

Effect of cardio myopeptidin on activity of CPK of coronary effluent of isolated rats with myocardial ischemia-reperfusion (n = 10, x ± s)

| | | Coronary effluent CPK (U/L) | | |
|---|---|---|---|---|
| Group | Dosage μg/ml | Prior ischemia | During ischemia | Perfusion |
| Pseudo-operation control | — | 15.3 ± 1.5 | 16.5 ± 1.8 | 17.1 ± 2.0 |
| Ischemia-reperfusion | — | 16.3 ± 2.3$^{\triangle}$ | 24.8 ± 2.7$^{\triangle\triangle\triangle}$ | 35.4 ± 4.3$^{\triangle\triangle\triangle}$ |
| Ischemia-reperfusion + cardio myopeptidin | 10 | 16.1 ± 2.6* | 20.7 ± 1.7*** | 22.7 ± 2.3*** |
| | 50 | 15.6 ± 1.7* | 17.9 ± 2.7*** | 19.0 ± 2.3*** |
| | 100 | 15.5 ± 2.7* | 15.3 ± 2.1*** | 16.5 ± 2.4*** |
| Ischemia-reperfusion + verapamil | 1 | 16.3 ± 2.0* | 16.2 ± 2.8*** | 16.0 ± 1.8*** |

Note:
Compared with pseudo-operation control group, $^{\triangle}P > 0.05$, $^{\triangle\triangle\triangle}P < 0.01$; compared with ischemia-reperfusion group, $*P > 0.05$, $***P < 0.01$.

TABLE 21

Effect of cardio myopeptidin on activity of LDH of coronary effluent of isolated rats with myocardial ischemia-reperfusion (n = 10, x ± s)

| | | Coronary effluent LDH (U/L) | | |
|---|---|---|---|---|
| Group | Dosage μg/ml | Prior ischemia | During ischemia | Perfusion |
| Pseudo-operation control | — | 11.8 ± 0.79 | 12.6 ± 1.1 | 11.8 ± 0.69 |
| Ischemia-reperfusion | — | 11.7 ± 0.83$^{\triangle}$ | 17.3 ± 1.9$^{\triangle\triangle\triangle}$ | 24.7 ± 1.7$^{\triangle\triangle\triangle}$ |
| Ischemia-reperfusion + cardio myopeptidin | 10 | 12.0 ± 0.58* | 13.4 ± 1.1*** | 15.3 ± 1.4*** |
| | 50 | 11.8 ± 0.53* | 12.9 ± 1.1*** | 13.4 ± 0.76*** |
| | 100 | 11.2 ± 0.55* | 12.2 ± 0.79*** | 12.9 ± 0.93*** |
| Ischemia-reperfusion + verapamil | 1 | 11.4 ± 0.78* | 13.0 ± 0.62*** | 14.3 ± 0.95*** |

Note:
Compared with pseudo-operation control group, $^{\triangle}P > 0.05$, $^{\triangle\triangle\triangle}P < 0.01$; compared with ischemia-reperfusion group, $*P > 0.05$, $***P < 0.01$.

Experiments indicated that cardio myopeptidin could obviously decrease the release of myocardial creatine phosphokinase, and the increase of activity of lactate dehydrogenase and contents of free fatty acid and malon dialhedyde caused by myocardial ischemia-reperfusion.

4. Effect of Cardio Myopeptidin on Myocardial Oxygen Consumption

Anesthetize dogs with sodium pentobarbital. Conduct endotracheal intubation and artificial respiration, and use an RM-86 polygraph to monitor electrocardiogram and aortic pressure. Open the thoracic cavity from the left side to expose the heart. Intubate a cannula from the apex of the heart to the left ventricle, and record the pressure of the left ventricle and pressure change rate (±dp/dt max). In order to know the change in circulation of the coronary artery and myocardial oxygen metabolism, separate the left circumflex branch of the coronary artery of dogs, use an electromagnetic flowmeter to measure the flow of coronary artery, and calculate the resistance against the coronary artery. Intubate a cannula from the external jugular vein of dogs to the coronary artery. Simultaneously draw the arterial blood and the coronary sinus blood. Use a blood gas analyzer (Model ABL-3, Denmark) to determine blood oxygen content, and calculate myocardial oxygen uptake and myocardial oxygen consumption. Keep the arterial blood pH, $CO_2$ and partial pressure of oxygen of dogs within normal range. The dose of MTP is 2.5 and 10 mg/kg, and the interval between two doses is 30 min. Continuously record various parameters after administration until they return to the control value. Take arterial blood and coronary sinus blood at 2, 5, 10 and 30 minutes after administration. Determine blood gas content, calculate myocardial oxygen uptake and myocardial oxygen consumption, and observe the effect of MTP on myocardial oxygen metabolism.

TABLE 22

Effect of cardio myopeptidin for intravenous injection on myocardial oxygen consumption and myocardial oxygen uptake in dogs (change value % after administration)

| Time(min) | myocardial oxygen consumption ($MVO_2$) | myocardial oxygen uptake ($O_2$ ext) |
|---|---|---|
| Cardio myopeptidin 2 mg/kg (N = 8) | | |
| 2 | −23.0 ± 26 | −4.00 ± 13 |
| 5 | −21.0 ± 13*** | 0 ± 8.0 |
| 10 | −18.0 ± 14 | −2.00 ± 6.0 |
| 20 | −9.00 ± 12 | −2.00 ± 12 |
| Cardio myopeptidin 5 mg/kg (N = 7) | | |
| 2 | −36.0 ± 24** | −5.00 ± 13 |
| 5 | −26.0 ± 21** | 6.00 ± 8.0 |
| 10 | −19.0 ± 15** | 6.00 ± 6.0* |
| 20 | −8.00 ± 10 | −14.0 ± 35 |
| Cardio myopeptidin 10 mg/kg (N = 6) | | |
| 5 | −22.0 ± 25 | 9.00 ± 5*** |
| 10 | −21.0 ± 14** | 2.00 ± 5.0 |
| 20 | −8.00 ± 4.0* | 3.00 ± 4.0 |
| 30 | −10.0 ± 7.0* | −6.00 ± 15 |
| Propranolol 2 mg/kg (N = 6) | | |
| 2 | −31.0 ± 13* | −3.00 ± 1.0 |
| 5 | −30.0 ± 13*** | 3.00 ± 7.0 |
| 10 | −33.0 ± 10*** | 3.00 ± 8.0 |
| 30 | −32.0 ± 14*** | 3.00 ± 9.0 |

Note:
Compared with that before administration: *$P > 0.05$, $P < 0.05$, *$P < 0.01$.

5. Effect of Cardio Myopeptidin on Myocardial Infarction

Anesthetize a healthy, grown male miniature pig with the body weight of 20.9±4.0 kg with 30 mg/kg of 3% sodium pentobarbital through auditory intravenous injection. Connect the tracheal cannula to a SC-3 electro-respirator to perform artificial positive pressure respiration. Open the thoracic cavity from the third rib at the left side to expose the heart. Separate the anterior descending branch of the coronary artery (about ⅓ distant from the apex of heart), and put a silk thread 0□ beneath it for ligation. Place a multi-point fixed type epicardium electrode with 20 points on the myocardial surface under the ligature. Record the myocardial electrical signals on an RTA-1200 model hot-wave recorder of a RM-6300 model eight-lead polygraph through a ZYS1-I model numerical control epicardium scanner and AB-601G bioelectric amplifier, and 1 mV standard voltage is equal to 1 mm. Under the control of the automatic timer, measure the change in the electrocardiogram at those 20 points. Intubate a cannula from the femoral artery to the abdominal aorta, and connect it to a AP-641G blood pressure amplifier through a TP-400T model pressotransduer to measure the mean blood pressure (MBP). Insert a needle electrode into the subcutaneous tissue of the four limbs, and use a AC-601G electrocardiogram amplifier to measure standard II-lead electrocardiogram (ECG□), and input the electrical signal of the ECG into an AT-601G cardiotachograph to measure the heart rate (HR). A femoral venous cannula is used for administration and fluid replacement.

In the experiment, the animals are divided into four groups and a total of 25 animals are experimented upon. When infusing 120 mg/kg of mannitol through phleboclysis for the control group, 5 animals die due to ventricular fibrillation, and 5 animals survive, so each of the other groups has five animals. They are respectively infused with 5 and 10 mg/kg experiment drug and 0.25 mg/kg positive drug verapamil through the femoral vein respectively. The dosage is 2 ml/kg, and the infusion rate is 2 ml/min. Trace the electrocardiogram after various indexes stabilize upon the completion of the operation. Ligate the anterior descending branch, then record the electrocardiogram after 5 min as the control before administration. Then administer the drug through phleboclysis. Record ECG II, MBR, HR and ST elevation values of the electrocardiogram at those 20 points respectively at 5, 10, 15, 20, 25, 30, 45, 60, 90, 120 and 180 min after the administration. Calculate the sum ST and take it as the index to measure the degree of myocardial ischemia. Set the point at which ST elevation of electrocardiogram exceeds 2 mV as the ischemic point, and calculate the total ischemic points (NST) as the index to measure the range of myocardial ischemia. At 3 h after the administration, bleed the animals to execute them and rapidly take out the heart. Cut out the ventricles and wash away the residual blood, and slice the ventricles under the location of ligature into 5 mm thick coronal-shape pieces. Keep the pieces away from light and dye them with 1% TTC at room temperature for 30 min. Then mark the ischemic region and non-ischemic region of both sides of 5 cardiac muscles on transparent film. Cut the film of the white infarct region and weigh. Use this weight to divide the weight of film of 10 sides of the ventricles, and use the result to calculate the percentage of infarct region in ventricular weight under the ligature.

Grouping, dosage and administration pattern of the experiment

| Group | Drug | Dose infused (mg/kg) | Infusion rate (ml/min) |
|---|---|---|---|
| Control group with solvent administered | Mannitol | 120 | 2 |
| Low-dose group of tested drug | cardio myopeptidin + mannitol | 5 + 120 | 2 |
| High-dose group of tested drug | cardio myopeptidin + mannitol | 10 + 120 | 2 |
| Control group with positive drugs administered | Verapamil | 0.25 | 2 |

TABLE 23

Effect of cardio myopeptidin for phleboclysis on scope of myocardial infarction in pigs

| Drug | Dose (mg/kg) | Animal number(n) | Infarction range (%) |
|---|---|---|---|
| Solvent control group | — | 5 | 19.4 ± 3.02 |
| cardio myopeptidin | 5 | 5 | 11.8 ± 3.13* |
| cardio myopeptidin | 10 | 5 | 10.2 ± 3.2** |
| Verapamil | 0.25 | 5 | 12.5 ± 3.4* |

Note:
Compared with solvent control group, *$P < 0.05$, **$P < 0.01$

It is demonstrated from the experiments that 5 and 10 mg/kg of cardio myopeptidin of the present invention can obviously lower ST of the electrocardiogram of pigs with myocardial infarction, decrease NST and reduce the scope of myocardial infarction. Cardio myopeptidin of the present invention has certain therapeutic action on arrhythmia and ventricular fibrillation (they may cause death) in pigs with acute myocardial ischemia, but poses no evident impact on blood pressure and heart rate.

EXPERIMENTAL EXAMPLE 3

This experiment involves the evaluation of human tolerance studies and safety studies of cardio myopeptidin for injection.

1. Research Methods 1.1 Single Intravenous Drip Test on Lyophilized Preparation of Cardio Myopeptidin for Injection General physical examination of 30 healthy male subjects to be tested is proved qualified. They are divided into five dose groups through the principle of selecting at random: 0.1 mg/kg(n=2), 0.4 mg/kg(n=4), 0.8 mg/kg(n=8), 1.6 mg/kg (n=8) and 3.2 mg(n=8). One subject produces rashes on cervical and thoracic regions when conducting the proposed highest dose test (3.2 mg/kg), which is judged as an anaphylactic response associated with the drug under test. Thus, the test is discontinued. According to the requirements of the scheme, the dose of lyophilized preparation of cardio myopeptidin for injection is reduced to 2.0 mg/kg as the highest dose group to continue the test.

The dosage is calculated according to the real body weight on each morning of the date on which the test starts. Subjects have breakfast at 7 am every day, and are administered lyophilized preparation of cardio myopeptidin for injection through intravenous drip from the forearm of the left upper extremity at 8 am. The drip rate is 3 ml/min.

Observe the symptoms, blood pressure, heart rate, respiration, electrocardiogram and ECG monitor before and after administration, and conduct routine blood examination, routine urine examination, blood biochemical examination and general physical examination.

1.2 Continuous Intravenous Drip Test on Lyophilized Preparation of Cardio Myopeptidin for Injection General physical examination of 16 healthy male subjects to be tested is proved qualified. They are divided into two dose groups: 1 mg/kg(n=8) and 2 mg/kg(n=8). The dosage is calculated according to the real body weight on each morning of the date on which the test starts. Subjects have breakfast at 7 am every day, and are administered with lyophilized preparation of cardio myopeptidin for injection through intravenous drip from the forearm of the left upper extremity at 8 am. The frequency is 1 time/day, and the drip rate is 3 ml/min. The administration of cardio myopeptidin continues for 7 days.

Observe the symptoms, blood pressure, heart rate, respiration, electrocardiogram and ECG monitoring on each day before and after administration, and conduct 24 h ECG monitoring on the first, third, fifth and seventh day. Perform routine blood examination, routine urine examination, blood biochemical examination and general physical examination on the third, fifth and eighth day.

2. Findings and Results 2.1 Single-administration Tolerance Test on Lyophilized Preparation of Cardio Myopeptidin for Injection 2.1.1 Thirty subjects take part in the test. Their average age is 22±2; average height is 170.8±5.9 cm; average body weight is 63.6±7.6 kg, and average body weight index is 21.8±1.5 kg/$M^2$.

30 subjects take part in the test of 6 dose groups, which are as follows:

Group 1: Dose: 0.1 mg/kg, Case number: 2 cases

Group 2: Dose: 0.4 mg/kg, Case number: 4 cases

Group 3: Dose: 0.8 mg/kg, Case number: 8 cases

Group 4: Dose: 1.6 mg/kg, Case number: 8 cases

Group 5: Dose: 2.0 mg/kg, Case number: 6 cases

Group 6: Dose: 3.2 mg/kg, Case number: 2 cases (1 case finishes the test, and 1 case discontinues the test).

2.1.2 No abnormality is found in the general physical examination of subjects among 29/30 cases who complete the tests of various doses.

2.1.3 The changes in blood pressure, heart rate, respiration, electrocardiogram examination at 5 min, 30 min, 60 min, 90 min, 2 h, 3 h, 8 h, 12 h and 24 h before and after administration and such observation indexes as routine blood examination, routine urine examination, hepatic and renal function, myocardial enzyme, blood fat, electrolytes, etc. are within the clinically allowable range. Parts of the indexes have statistical differences ($P<0.05$ or $P<0.01$), but they have no clinical significance.

2.1.4 3/30 subjects produce adverse reaction irrelevant with the drug under test.

(1) 2/8 cases in Group 4 (dose is 1.6 mg/kg) present light distending pain at the injection site, and no treatment is conducted to allow spontaneous disappearance.

(2) 1/2 cases in Group 6 (dose is 3.2 mg/kg) develop red rashes on head, cervical, upper thoracic and upper back regions 30 min after administration (real dosage is about 90 mg/planned dosage is 221mg). They have no protrusion, and their color fades when pressing them, diffused to form flakes. Thus, these rashes are judged "very likely associated with drugs under test," and injection of the drug stops. Rashes spontaneously disappear 3 h after suspension of the drugs, and subjects have no chief complaints of discomfort.

2.2 Continuous-administration Tolerance Test on Lyophilized Preparation of Cardio Myopeptidin for Injection 2.2.1. According to the scheme and with regard of the single-administration test results, 16 subjects take part and complete the tests of two dose groups. They are administered with lyophilized preparation of cardio myopeptidin for injection through intravenous drip. The frequency is 1 time/day, and the administration is conducted for 7 consecutive days.

| | |
|---|---|
| Group 1: Dose: 1.0 mg/kg × 7 days | Case number: 8 cases |
| Group 2: Dose: 2.0 mg/kg × 7 days | Case number: 8 cases |

2.2.2. Physical examination is conducted on the 3rd, 5th and 8th days after administration, and no abnormality is found among all subjects.

2.2.3. Observe the symptoms, blood pressure, heart rate, respiration, electrocardiogram of each day before and after administration. Conduct 24 h ECG monitoring on the first, third, fifth and seventh day, and perform routine blood examination, routine urine examination, hepatic and renal function, myocardial enzyme, blood fat, electrolytes and general physical examination on the third, fifth and eighth day. The changes in all observation indexes are within the clinically allowable range, part of the indexes have statistical differences ($P<0.05$ or $P<0.01$), but they have no clinical significance.

2.2.4. CK (creatine phosphokinase) of the two dose groups and CK□MB (creatine phosphokinase isoenzyme) of 2.0 mg/kg dose group are found obviously decreased in blood biochemical examination at 3, 5 and 8 days after administration ($P<0.01$). LDH (loctate dehyrogenase) and LDH□1 (lactic dehydrogenase isoenzyme 1) of the two dose groups after administration also have similar falling tendency.

2.2.5. Among 5/8 cases of the 2.0 mg/kg dose group, when administering drugs under test through intravenous drip, 2-7 cases present such adverse reaction symptoms as distending pain, aching pain, pain in the left arm etc at the transfusion site associated with drugs under test. No measurements were taken for the 2 cases and the symptoms disappear spontaneously. The symptoms of 3 cases disappear after lowering the drip rate.

3. Conclusion 3.1. Healthy male subjects produce good tolerance in a single intravenous drip of lyophilized preparation of cardio myopeptidin for injection within the dose range from 0.1 to 2.0 mg/kg.

3.2 Continuous intravenous drip of lyophilized preparation of cardio myopeptidin for injection is conducted for healthy male subjects, the frequency is once daily, and the administration lasts for consecutive 7 days. The 1.0 mg/kg dose group produces good tolerance, without adverse reaction. Some of the subjects in 2.0 mg/kg dose group develop aching pain and discomfort in consecutive administration, but they can be tolerated, and no subjects discontinue the administration.

3.3. The changes in such general physical examination as blood pressure, heart rate and respiration, and electrocardiogram, 24 h ECG monitoring, and such examination indexes as routine blood examination, routine urine examination, hepatic and renal function, myocardial enzyme, blood fat, electrolytes. etc. before and after single administration and continuous administration are within the clinically allowable range. Parts of the indexes have statistical differences ($P<0.05$ or $P<0.01$), but they have no clinical significance.

3.4. 5/8 cases of 2.0 mg/kg dose group present with aching pain, distending pain, algaesthesis at the administration site, and such symptoms can disappear after lowering the drip rate. This indicates this preparation may have local stimulation, and the drip rate shall be adjusted as required during the intravenous drip.

3.5. During the continuous administration test, laboratory examination shows part of myocardial enzyme indexes have shown falling tendency after administration, and it shall be verified in the Phase II clinical trial whether such tendency prompts its drug effect.

3.6. Persons once allergic to biological products shall take this drug with caution, but symptoms will disappear spontaneously after discontinuation of administration.

EXPERIMENTAL EXAMPLE 4

Preliminary Stability Test on Cardio Myopeptidin

1. The results of influencing factor test and accelerated test on cardio myopeptidin for injection show, after the external packaging is removed, the appearance rapidly turns yellow under the conditions that humidity is more than 75% and temperature exceeds 37° C., moisture content increases and activity decreases.

2. The result of room-temperature filed sample inspection shows, except the appearance turns light yellow after 480~540 days, other test items present no change, and various test items have no change if the drug is stored at 4° C. This demonstrates cardio myopeptidin can be stored for 150 days at least at room temperature under the situation in which humidity is 45%~90%, and characteristics of its appearance, content and activity fail to show change, and it can be stored at 4° C. for 480 days at least.

EXPERIMENTAL EXAMPLE 5

This example relates to the quality standard of cardio myopeptidin for injection.

This invention is a polypeptide active substance isolated from healthy infant pigs with molecular weight less than 10000 Da. After adding a proper amount of mannitol as excipient, it is made into a sterile product through lyophilization with the polypeptide content from 90.0% to 110.0% of the labeled amount.

1. Characteristics: cardio myopeptidin for injection of this invention is off-white or yellowish lyophilized cakes or powder.

2. Identification:

(1). Take cardio myopeptidin for injection quantum satis (q.s.), to which water is added to make into a solution such that each ml contains 5 mg of polypeptide. Add 2 ml biuret reagent to the solution, and mix well; then a purple solution is produced immediately.

[Preparation of biuret reagent: dissolve 0.75 g copper sulphate ($CuSO_4.5H_2O$) and 3 g potassium sodium tartrate (NaKC$_4$H$_4$O$_6$.4H$_2$O) with about 250 ml, add 150 ml of 10% sodium hydroxide test solution under agitation and dilute with water to 500 ml, then store the solution in a plastic bottle.]

(2). Take cardio myopeptidin for injection q.s., to which water is added to make into a solution such that each ml contains 50 μg polypeptide. Determine polypeptide content as directed under spectrophotography (Appendix A, Volume II of CP2000). There is a maximum absorption at the wavelength of 200±2 nm.

(3). Take cardio myopeptidin for injection q.s., to which water is added to make into a solution such that each ml contains 5 mg of polypeptide. Measure 1 ml from the solution, to which 0.5 ml of ferricchloride test solution and 0.5 ml of sodium hydroxide test solution respectively are added. A brown precipitate is produced immediately and does not disappear after shaking. Addition of excess sodium hydroxide test solution to it will dissolve it into a brown solution.

(4). Take cardio myopeptidin for injection and the reference substance, to which mobile phase is added to make a 1 mg/ml solution. Allow it to dissolve completely and determine with HPLC method. Comparing this product with the reference substance, the difference between relative retention time of principal peaks 1, 4 and 5 does not exceed 0.1 min.

3. Tests

Acidity: Take cardio myopeptidin for injection q.s. in bottles, add water in each bottle to make into a solution that each ml contains 5 mg polypeptide, mix the solutions and conduct determination according to the stipulated method (Appendix H, Volume II of CP2000). The pH value shall be 6.0~7.0.

Moisture: Take cardio myopeptidin for injection and determine moisture according to the method for determination of moisture (Appendix M, Method 1, Volume II of CP2000). Moisture content shall not exceed 1.5%.

Protein: To a suitable amount of cardio myopeptidin for injection, add water to obtain a solution where each ml contains 2.5 mg of polypeptide. Take 2 ml of the solution and add 1 ml of 20% sulfosalicylic acid, No turbidity shall appear.

Color of solution: To a suitable amount of cardio myopeptidin for injection, add water to obtain a solution where each ml contains 1 mg of polypeptide, and determine the color according to the stipulated method (Appendix A, Volume II of CP2000). The color of solution in the test tube shall be not more intense than that of the yellow tube.

Clarity: To a suitable amount of cardio myopeptidin for injection, add water to obtain a solution where each ml contains 2.5 mg of polypeptide, and check the clarity according to the stipulated method (Appendix B, Volume II of CP 2000). The solution shall be clear. Any turbidity if produced should not be more intense when compared with No. 1 standard turbidity solution.

Molecular weight: Proceed with the high-performance liquid chromatography (Appendix V D, Volume II of CP 2000). The average molecular weight of this product shall not exceed 10000 Da.

Nucleic acid: To a suitable amount of cardio myopeptidin for injection, add water to obtain a solution where each ml contains 2.5 mg of polypeptide, and determine nucleic acid content according to the method for the determination of ribose. Ribonucleic acid content of each bottle shall not exceed 0.8% of the labeled amount, and deoxyribonucleic acid content of each bottle shall not exceed 3% of the labeled amount.

Sterility: To a suitable amount of cardio myopeptidin for injection, add sodium chloride injection solution to obtain a solution where each ml contains 5 mg of polypeptide, and carry out sterility test according to the stipulated method (Chinese Requirements for Biological Product Version 2000, P29, Volume I of Chinese Requirements for Biologics, Edition 2000). The result shall comply with relevant requirements.

Pyrogen: To a suitable amount of cardio myopeptidin for injection, add sodium chloride injection solution to obtain a solution where each ml contains 5 mg of polypeptide, and carry out the pyrogen test according to the stipulated method (Volume 2, Appendix D, Volume II of CP2000). The dose should be 1 ml/kg body weight of rabbits, and the result shall comply with relevant requirements.

Hypersensitivity test: Take 6 guinea pigs each with a body weight of 250~350 g, inject 0.5 ml of this product for 3 consecutive times with the interval of one day (add sodium chloride injection solution to dissolve the drug into a solution that each ml contains 2.5 mg of polypeptide), and administer 1 ml of this product through intravenous injection after two weeks and observe for 15 min. No anaphylactic response shall appear. If two or more of such phenomena as piloerection, dyspnea, sneezing, retching or three coughs or one of such phenomena as rale, tic, collapse or death, etc. appear, it shall be interpreted as positive.

Abnormal toxicity: Add sodium chloride injection solution to this product to obtain a solution where each ml contains 2.5 mg of polypeptide, and test the abnormal toxicity according to the stipulated method (Appendix C, Volume II of CP2000). Route of administration shall be intravenous injection, and the result shall comply with relevant requirements.

Depressor substance: Add sodium chloride injection solution to this product to obtain a solution where each ml contains 1.0 mg of polypeptide, and test the depressor substance according to the stipulated method (Appendix G of CP2000). The dose should be 0.1 mg per kg body weight of cats, and the result shall comply with relevant requirements.

Activity: Take cardio myopeptidin for injection q.s., and determine its activity according to the method for the determination of activity. Activity of this product shall not be less than 2.2.

Others: Shall be concordant with various associated provisions for injection (Appendix I B, Volume II of CP2000).

4. Drug Content Determination:

To a suitable amount of cardio myopeptidin for injection, add water to obtain a solution where each ml contains about 0.1 mg of polypeptide, and assay according to the Folin-phenol method.

Embodiment 1

1 kg of ventricular myocardium of healthy infant pigs is cleaned and minced; 1 kg of sterile distilled water is added to the minced ventricular myocardium to homogenize under the rotation speed of 3000 rpm/min. The homogenate is frozen at −20° C. for 24 h subsequently melted, then the homogenat is heated to 75° C. in a water bath after the homogenate is frozen and thawed, repeating 3 times. The heated homogenate is filtered with a XAS03-172/8 plate-and-frame filter (purchased from Guangzhou Medicinal Apparatus Research Institute) with pores of 10μ of medium-speed filter paper to obtain the coarse filtrate, and the residue is discarded. The coarse filtrate is ultrafiltered by a hollow-fiber column (specification of F60, purchased from Sweden Gambro Corporation) to obtain the fine filtrate with the molecular weight of 12 Kd. The fine filtrate is ultrafiltered by ultrafiltration membrane (10 Kd, Millipore Corporation) wherein 150 ml of cardio myopeptidin solution with the molecular weight of 9500 Da is intercepted. The obtained cardio myopeptidin solution is concentrated with a reverse osmosis and concentration column provided by Millipore Corporation.

The cardio myopeptidin solution is inspected for quality until it meets the quality standard, then a aseptic filtration, filling and lyophilization (lyophilizer is used) is performed respectively. The procedure of lyophilization comprises the steps of: the shelf in the drying chamber is cooled down to −20° C. in 20 minutes. The cardio myopeptidin solution is then frozen to −35° C. in 30 minutes and stands for 2 hours in such condition. The temperature within the condenser is chilled to −50° C., then the pressure is reduced until the vacuum degree reaches 100 Kpa. The drying chamber is connected with the condenser, and the refrigeration of the drying chamber is stopped, when vacuum degree of the drying chamber reaches 15 Pa, the temperature in the drying chamber is increased to 15° C. at the rate of 3° C./min and kept for 3 hours, and the temperature is raised continuously to 22° C. at the rate of 10° C./min and maintained for 5 hours. Then the temperature is raised continuously to 35° C. at the rate of 10° C./min and kept for 2 hours, whereafter the temperature is raised to 50° C. at the rate of 5° C./min for 1 h. Then in the cooling stage, the temperature is reduced to 40° C. within 20 min and maintained for 10 hours. Thus, lyophilized cardio myopeptidin with qualified appearance is obtained, and the product is taken out for sealing.

It is shown by analysis that the polypeptide content of the obtained cardio myopeptidin is 85%, free amino acid content is 8%, ribonucleic acid content is 1%, deoxyribonucleic acid content is 6%, and the average molecular weight is 9500 Da.

Embodiment 2

1 kg of ventricular myocardium from healthy infant cattle is cleaned and minced, and 1 kg of sterile distilled water is added to the minced ventricular myocardium to homogenize under the rotation speed of 5000 rpm/min. The homogenate is frozen at −30° C. for 48 h subsequently melted, then the homogenate is heated to 90° C. at a water bath after the homogenate is frozen and thawed, repeating 4 times. The heated homogenate is filtered with a XAS03-172/8 plate-and-frame filter (purchased from Guangzhou Medicinal Apparatus Research Institute) with pores of 8μ of medium-speed filter paper to obtain the coarse filtrate, and the residue is discarded. The coarse filtrate is ultrafiltered by a hollow-fiber column (specification of F60, purchased from Sweden Gambro Corporation) to obtain the fine filtrate with the molecular weight of 12 Kd. The fine filtrate is ultrafiltered by ultrafiltration membrane (5 Kd, Millipore Corporation) wherein 150 ml of cardio myopeptidin solution with the molecular weight of 5000 Da is intercepted. The obtained cardio myopeptidin solution is concentrated with a reverse osmosis and concentration column provided by Millipore Corporation.

The cardio myopeptidin solution is inspected for quality until it meets the quality standard, then an aseptic filtration, filling and lyophilization (the equipment used is a lyophilizer) is performed respectively. The procedure of lyophilization comprises the steps of: the shelf in the drying chamber is cooled down to −18° C. in 40 minutes. The cardio myopeptidin is then frozen to −25° C. in 20 minutes, maintaining at this temperature for 1 hour. Then the condenser is chilled to −40° C., then the pressure is reduced until the vacuum degree reaches 95 Kpa. The drying chamber is connected with the condenser, and the refrigeration of the drying chamber is stopped, when the vacuum degree of the drying chamber reaches 12 Pa, the temperature of the drying chamber is raised to 10° C. at the rate of 2° C./min and maintained for 5 hours. The temperature is raised continuously to 25° C. at the rate of 16° C./min and maintained for 5 hours. Then the temperature is raised continuously to 35° C. at the rate of 10° C./min and maintained for 3 hours, whereafter the temperature is raised to 60° C. at the rate of 8° C./min and maintained for 2 h. Then in the cooling stage, the temperature is reduced to 46° C. within 30 min and maintained for 8 hours. Thus, lyophilized cardio myopeptidin with qualified appearance is obtained, and the product is taken out for sealing.

Through analysis for cardio myopeptidin obtained in this embodiment, its polypeptide content is 78%, free amino acid content is 15%, ribonucleic acid content is 2%, deoxyribonucleic acid content is 5%, and the average molecular weight is 5000 Da.

Embodiment 3

1 kg of ventricular myocardium from healthy infant rabbits is cleaned and minced, and 1 kg of sterile distilled water is added to the minced ventricular myocardium to homogenize under the rotation speed of 1000 rpm/min. The homogenate is frozen at −10° C. for 72 h and subsequently melted, then the homogenate is heated to 85° C. in a water bath after the homogenate is frozen and thawed, repeating 3 times. The heated homogenate is filtered with a XAS03-172/8 plate-and-frame filter (purchased from Guangzhou Medicinal Apparatus Research Institute) with pores of 5μ of medium-speed filter paper to obtain the coarse filtrate, and the residue is discarded. The coarse filtrate is ultrafiltered by a hollow-fiber column (specification of F60, purchased from Sweden Gambro Corporation) to obtain the fine filtrate with the molecular weight of 11 Kd. The fine filtrate is ultrafiltered by ultrafiltration membrane (3 Kd, Millipore Corporation) wherein 150 ml of cardio myopeptidin solution with the molecular weight of 2000 Da is intercepted. The obtained cardio myopeptidin solution is concentrated with a reverse osmosis and concentration column provided by Millipore Corporation.

The quality inspection is performed with the cardio myopeptidin solution until it meet the quality standard, then a aseptic filtration, filling and lyophilization (the equipment used is a lyophilizer) is performed respectively. The procedure of lyophilization comprises the step of: the shelf in the drying chamber is cooled down to −15° C. in 10 minutes, then the cardio myopeptidin solution is cooled down to −30° C. in 25 minutes and the temperature is maintained for 2.5 hours. The temperature within the condenser is cooled down to −45° C., then the pressure is reduced until the vacuum degree reaches 90 Kpa. The drying chamber is connected with the condenser, and the refrigeration of the drying chamber is stopped, when the vacuum degree of the drying chamber reaches 10 Pa, the temperature in the drying chamber is raised to 5° C. at the rate of 5° C./min and maintained for 6 hours, and the temperature is raised continuously to 15° C. at the rate of 8° C./min and maintained for 8 hours, then the temperature is raised continuously to 32° C. at the rate of 7° C./min and maintained for 4 hours, whereafter the temperature is raised to 55° C. at the rate of 4° C./min and stayed for 3 h. Then in the cooling stage, the temperature is reduced to 50° C. within 10 min. and maintained at such temperature for 15 hours. Thus, lyophilized cardio myopeptidin with qualified appearance is obtained, and the product is taken out for sealing.

It is shown by analysis that the polypeptide content of obtained cardio myopeptidin is 90%, free amino acid content is 6%, ribonucleic acid content is 1%, deoxyribonucleic acid content is 3%, and average molecular weight is 2000 Da.

Embodiment 4

Identical with Embodiment 1, the difference is that cardio myopeptidin solution with intercepted molecular weight of 4000 Da is tested up to the quality standard through quality inspection, then subjected to aseptic filtration and filling, and is prepared according to the following procedure:

composition:

| | |
|---|---|
| cardio myopeptidin | 20 mg |
| mannitol | 375 mg |
| activated carbon | 0.005 mg |
| water for injection | Add to 5 ml |

Fill the solution into bottles and place them in a lyophilizer. Cool down the shelf in the drying chamber to −20° C. in 30 minutes, then after 40 minutes cool down the product to −35° C. and maintain at such temperature for 3 hours. Cool down the temperature within the condenser to −50° C., then reduce the pressure. Connect the drying chamber and the condenser when the vacuum degree reaches 95 Kpa, and stop the refrigeration of the drying cabinet, begin to raise the temperature to 10° C. at the rate of 3° C./min, and incubate for 4 hours when vacuum degree of the drying cabinet is 15 Pa. Continue to raise the temperature to 20° C. at the rate of 12° C./min, maintained for 5.5 hours. Continue to raise the temperature to 30° C. at the rate of 12° C./min, maintain for 1.5 h. Continuously raise the temperature to 60° C. at the rate of 6° C./min, maintain for 2 h. Then in the cooling stage, cool down the temperature to 48° C. within 20 min and maintain at such temperature for 9 hours. Thus, obtain the lyophilized cardio myopeptidin product with qualified appearance. Take out the product and seal.

Through lyophilization, the finished product with cardio myopeptidin content of 2.0 mg/ml is obtained. Through analysis for said cardio myopeptidin, its polypeptide content is 80%, free amino acid content is 12%, ribonucleic acid content is 2%, deoxyribonucleic acid content is 6%, and the average molecular weight is 4000 Da.

Embodiment 5

A essentially identical process is performed according to Embodiment 1. The difference is that the raw material is the ventricular myocardium of healthy infant horses, and the cardio myopeptidin solution with intercepted molecular weight of 8000 Da is obtained. Analysis indicated that the polypeptide content of cardio myopeptidin is 84.5%, free amino acid content is 6%, ribonucleic acid content is 2%, deoxyribonucleic acid content is 7.5%, and average molecular weight is 8000 Da.

Embodiment 6

A essentially identical process is performed according to Embodiment 1. The difference is that cardio myopeptidin solution further comprises trehalose, and the component ratio is: 15 mg/ml cardio myopeptidin: 200 mg/ml trehalose.

Embodiment 7

A essentially identical process is performed according to Embodiment 1. The difference is that the raw material is the ventricular myocardium of healthy pigs, the cardio myopeptidin solution further comprises lactose, and the component ratio is: 18 mg/ml cardio myopeptidin: 250 mg/ml lactose.

Embodiment 8

A essentially identical process is performed according to Embodiment 4. The difference is that cardio myopeptidin solution with intercepted molecular weight of 1000 Da is obtained, and the components of cardio myopeptidin solution are:

| | |
|---|---|
| cardio myopeptidin | 16 mg |
| sucrose | 300 mg |
| activated carbon | 0.005 mg |
| water for injection | Add to 5 ml |

Analysis indicated that the polypeptide content of cardio myopeptidin is 82%, free amino acid content is 12%, ribonucleic acid content is 2%, deoxyribonucleic acid content is 4%, and the average molecular weight is 1000 Da.

We claim:

1. A method of preparing a cardio myopeptidin from hearts of healthy non-human mammals comprising the steps of:
   (a) cleaning and cutting the hearts of healthy non-human mammals;
   (b) homogenizing the hearts by adding sterile distilled water to the myocardium of the hearts of healthy non-human mammals which is cleaned and cut, thereby creating homogenate;
   (c) freezing and thawing the homogenate for 3 to 4 cycles;
   (d) heating the homogenate to 65 to 95° C.;
   (e) filtering the homogenate using a plate-and-frame filter to obtain a coarse filtrate, and removing a residue resulting from the filtering;
   (f) ultra-filtering the coarse filtrate with a hollow-fiber column to obtain a fine filtrate having a molecular weight of less than 12000 Da;
   (g) ultra-filtering the fine filtrate using an ultrafiltration membrane to obtain the cardio myopeptidin solution with a molecular weight in the range from 2000 to 8000 Da; and
   (h) concentrating the cardio myopeptidin solution by reverse osmosis to obtain a concentrated cardio myopeptidin solution;
   (i) testing the quality of concentrated cardio myopeptidin solution; and,
   (j) filtering aseptically, filling, and lyophilizing the concentrated cardio myopeptidin solution to obtain a solution comprising: 75% to 90% of cardio myopeptidin; 6% to 15% of free amino acid; less than 2% of ribonucleic acid; and, less than 7.5% of deoxyribonucleic acid, wherein the cardio myopeptidin shows four to five principal peaks on an HPLC analysis spectrum, having a relative peak area of more than 85%, and wherein the cardio myopeptidin reduces the effect of ischemia reperfusion in the heart.

2. The method of claim 1 wherein a weight average of the molecular weight is in the range from 2000 to 5000 Da.

3. The method of claim 1 wherein the non-human mammals is infant mammals comprising pigs, cattle, sheep, rabbits, or horses.

4. The method of claim 1 wherein an isoelectrofocusing electrophoresis of the cardio myopeptidin displays 2 to 6 stained bands; wherein the cardio myopeptidin has a stable maximum absorption peak at 190 to 210 nm wavelength within a UV spectrum, and wherein the cardio myopeptidin shows five peaks on an FPLC analysis spectrum, with a sum of relative area from 90% to 95%.

5. The method of claim 1 wherein the cardio myopeptidin shows five principal peaks on an HPLC analysis spectrum; the sum of the relative percentage of principal peaks 1, 4 and 5 is more than 66%, and the proportion of the relative retention time of principal peaks 1, 4 and 5 is 1:1.61:2.14 (±0.1).

6. The method of claim 1 wherein the sterile distilled water is added in an amount from 0.5 to 4 times that of the myocardium of the mammals, and wherein the step of homogenizing comprises rotating at a rotation speed in the range of from 1000 to 5000 rpm/min.

7. The method of claim 1 wherein the freezing step is performed at a temperature of less than about −5° C. for 24 to 72 hours; and wherein the heating step comprises water bath heating or direct heating at a temperature of 70 to 90° C. for not more than 2 hours.

8. A method of using the cardio myopeptidin prepared by the method of claim 1 comprising the step of preparing a medicament for the treatment of cardiovascular disease or myocardial ischemia-reperfusion injuries.

* * * * *